(12) United States Patent
Glick et al.

(10) Patent No.: US 6,211,360 B1
(45) Date of Patent: Apr. 3, 2001

(54) IBOGAMINE CONGENERS

(75) Inventors: Stanley D. Glick, Delmar, NY (US); Martin E. Kuehne, Burlington, VT (US)

(73) Assignees: Albany Medical College, Albany, NY (US); University of Vermont, Burlington, VT (US)

( * ) Notice: Subject to any disclaimer, the term of this patent is extended or adjusted under 35 U.S.C. 154(b) by 0 days.

(21) Appl. No.: 09/011,809

(22) PCT Filed: Aug. 2, 1996

(86) PCT No.: PCT/US96/12627

§ 371 Date: Aug. 31, 1998

§ 102(e) Date: Aug. 31, 1998

(87) PCT Pub. No.: WO97/05869

PCT Pub. Date: Feb. 20, 1997

Related U.S. Application Data

(60) Provisional application No. 60/002,048, filed on Aug. 8, 1995.

(51) Int. Cl.[7] ............... C07D 487/18; C07D 487/08; A61K 31/33

(52) U.S. Cl. ..................................... 540/477; 514/183

(58) Field of Search ................ 540/477; 514/183

(56) References Cited

U.S. PATENT DOCUMENTS

| | | | |
|---|---|---|---|
| 3,681,362 | 8/1972 | Nagata et al. | 514/214 X |
| 4,499,096 | 2/1985 | Lotsof | 514/214 |
| 4,587,243 | 5/1986 | Lotsof | 514/214 |
| 4,769,453 | 9/1988 | Potier et al. | 540/478 |
| 5,152,994 | 10/1992 | Lotsof | 424/436 |

OTHER PUBLICATIONS

Azoug et al, Phytochemistry, vol. 39, No. 5, pp. 1223 to 1228, Jul. 1995.*

Glick et al, Brain Research, vol. 657, pp. 14 to 22, Sep. 1994.*

Deecher et al, Brain Research, vol. 571, pp. 242 to 247, Dec. 1992.*

Singbartl et al., "Structure–Activity Relationships of Intracerebrally Injected Tremorigenic Indole Alkaloids," *Neuropharmacology*, 12:239–244 (1973).

Kan et al., "Détermination de Structures par RMN du H á 400 MHz: Albifloranine, un Nouvel Alcaloïde de Tabernaemontana Albiflora," *Journal of Medicinal Plant Research*, 41:72–74 (1981).

Glick et al., "Effects and Aftereffects of Ibogaine on Morphine Self–Administration in Rats," *European Journal of Pharmacology*, 195:341–345 (1991).

Bornmann et al., "A Common Intermediate Providing Syntheses of Ψ–Tabersonine, Coronaridine, Iboxyphylline, Ibophyllidine, Vinamidin, and Vinblastine," *J. Org. Chem.*, 57:1752–1760 (1992).

Kuehne et al., "Formation of D–Nor Aspidosperma Alkaloids by Condensation of $N^b$–Benzylindoloazepine with Aldehydes," *J. Org. Chem.*, 58:4147–4148 (1993).

O'Hearn et al., "Ibogaine Neurotoxicity Raises New Questions In Addiction Research," *The Journal of NIH Research*, 5:50–55 (1993).

Saxton, "The Ibogamine–Catharanthine Group," in Saxton, ed., *The Monoterpenoid Indole Alkaloids*, John Wiley & Sons Ltd., pp. 487–521 (1994).

\* cited by examiner

*Primary Examiner*—Floyd D. Higel
(74) *Attorney, Agent, or Firm*—Nixon Peabody LLP

(57) ABSTRACT

The present invention is directed to compounds having formula (1), wherein n is from 0 to 8; $R^1$ is $CH_2OH$, $CH(OH)R^5$, $CH_2OR^5$, $CO_2R^5$, $C(O)NH_2$, $C(I)NHR^5$, $C(O)NR^5R^6$, $C(O)NHNH_2$, $C(O)NHNHR^5$, $C(O)NHNR^5R^6$, $C(O)NR^5NH_2$, $C(O)NR^5NHR^6$, $C(O)NR^5NR^6R^7$, $C(O)NHNH(C(O)R^5)$, $C(O)NHNR^5(C(O)R^6)$ $C(O)NR^5NH(C(O)R^6)$, $C(O)NR^5NR^6(C(O)R^7)$, CN, or $C(O)R^5$; $R^2$ is H, unsubstituted or substituted alkyl, YH, $YR^8$, $YC(O)R^8$, $C(O)YR^8$, $C(O)NH_2$, $C(O)NHR_8$, $C(O)NR^8R^9$, $NH_2$, $NHR^8$, $NR^8R^9$, $NHC(O)R^8$, or $NR^8C(O)R^9$; $R^3$ and $R^4$ are the same or different and are selected from the group consisting of H, halogens, unsubstituted or substituted alkyl, OH, $OR^{10}$, $NH_2$, $NHR^{10}$, $NR^{10}R^{11}$, $NHC(O)R^{10}$, or $NR^{10}C(O)R^{11}$; $R^5$, $R^6$, $R^7$, $R^8$, $R^9$, $R^{10}$, and $R^{11}$ are the same or different and are selected from the group consisting of unsubstituted alkyl and substituted alkyl and substituted alkyl; $R^{12}$ is selected from the group consisting of J, unsubstituted alkyl, and substituted alkyl; and Y is O or S; provided that when n is O, $R^2$ is selected from the group consisting of H, substituted alkyl, and unsubstituted alkyl; and pharmaceutically acceptable salts thereof. The compounds are useful in the treatment of subjects addicted to opiates and stimulants and have reduced side effects relative to other ibogamine congeners.

(1)

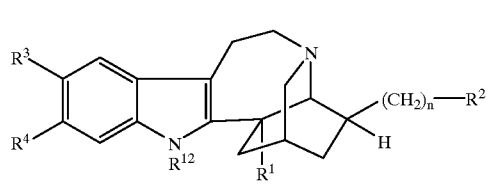

54 Claims, 8 Drawing Sheets

IBOGAMINE CONGENERS

This application is the National Stage of International application No. PCT/US96/12627 filed Aug. 2, 1996, and claims the benefit of U.S. Provisional Patent Application Ser. No. 60/002,048, filed Aug. 8, 1995.

This invention was made with the support of the National Cancer Institute (Grant No. CA 12010) and the National Institute for Drug Abuse (Grant No. DA 03817). The Federal Government may retain certain rights in the invention.

FIELD OF THE INVENTION

The present invention relates to ibogamine congeners and to methods for treating addictive behavior.

BACKGROUND OF THE INVENTION

Throughout this application various publications are referenced, many in parenthesis. Full citations for these publications are provided at the end of the Detailed Description. The disclosures of these publications in their entireties are hereby incorporated by reference in this application.

Ibogaine is one of several alkaloids found in the root bark of the African shrub *Tabernanthe iboga*. It has a ring skeleton common with ibogamine and has been identified as a potential interrupter of addictive behavior.

Male members of the Mitsogho people in Gabon ingest scrapings of the iboga root as part of the initiation rite into the Bwiti, a secret society of men. The rite of passage, which continues for several days, begins with a period of violent vomiting, followed by periods of drowsiness, motor incoordination, agitation, tremor, progression through a dream state, and, finally, sleep. The rite is thought to constitute an encounter with higher spiritual entities.

People who have taken purified ibogaine as an experimental drug report a similar sequence of events lasting three days, including visions, periods of high energy accompanied by flashes of light, and, eventually, sleep. Upon waking, many drug addicts reportedly lose their craving for addictive drugs over extended periods of time.

U.S. Pat. Nos. 4,499,096, 4,587,243, and 5,152,994, all to Lotsof, report that ibogaine is effective in treating opiate (heroin), stimulant (cocaine and amphetamine), nicotine, caffeine, and alcohol addictions. The treatment supposedly interrupts the physiological and psychological aspects of addiction and eliminates the desire to use drugs. In both opiate and stimulant syndromes, a single oral treatment with ibogaine or its salts, in dosages of 6 to 19 mg/kg, is said to be effective for about 6 months, and a series of four treatments is said to eliminate addictive behavior for approximately 3 years. Using an animal model of drug addiction, several studies have sought to determine whether these claims can be substantiated under controlled conditions. In one preliminary study [1], ibogaine dose-dependently decreased morphine self-administration in the hour after ibogaine treatment (acute effect) and to a lesser but significant extent, a day later (aftereffect). In some rats there was a persistent decrease in morphine intake for several days or weeks after a single injection of ibogaine, whereas other rats began to show such persistent changes after two to three weekly injections, and a few rats appeared to be entirely resistant to prolonged aftereffects. Similar effects of ibogaine on cocaine self-administration in rats were recently reported by Cappendijk and Dzoljic [2].

In humans, as in rats, ibogaine's efficacy as an anti-addictive therapy appears to vary substantially from one individual to another even the most ardent supporters of ibogaine's usefulness would probably concede that at least 30% of treated addicts do not decrease their drug intake.

Ibogaine also exhibits several side effects that limit its therapeutic utility. For example, the compound exhibits undesirable stimulant and hallucinogenic properties. In addition, ibogaine induces tremors. Very similar tremors are induced by harmaline, another natural alkaloid that is chemically related to ibogaine but derived from a different plant (*Peganum harmala*). Both ibogaine- and harmaline-induced tremors appear to be due to activation of an olivo-cerebellar pathway [3–5], and, in rats, high doses of both agents have recently been shown to damage the cerebellar vermis, presumably as a result of overstimulation of cerebellar Purkinje cells [5,6]. In addition ibogaine has an acute effect on motivated behavior during the first hour immediately following administration, as indicated by severely reduced bar pressing for water.

In view of the serious health effects and negative societal effects associated with addictive behavior, and the side effects of ibogaine treatment, the need continues for compounds which reduce addiction to addictive substances. The present invention is directed to overcoming this deficiency in the art.

SUMMARY OF THE INVENTION

The present invention relates to a compound having the formula:

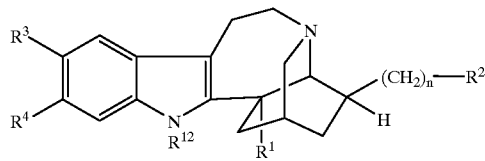

wherein
n is from 0 to 8;
$R^1$ is $CH_2OH$, $CH(OH)R^5$, $CH_2OR^5$, $CO_2R^5$, $C(O)NH_2$, $C(O)NHR^5$, $C(O)NR^5R^6$, $C(O)NHNH_2$, $C(O)NHNHR^5$, $C(O)NHNR^5R^6$, $C(O)NR^5NH_2$, $C(O)NR^5NHR^6$, $C(O)NR^5NR^6R^7$, $C(O)NHNH(C(O)R^5)$, $C(O)NHNR^5(C(O)R^6)$, $C(O)NR^5NH(C(O)R^6)$, $C(O)NR^5NR^6(C(O)R^7)$, CN, or $C(O)R^5$;
$R^2$ is H, unsubstituted or substituted alkyl, YH, $YR^8$, $YC(O)R^8$, $C(O)YR^8$, $C(O)NH_2$, $C(O)NHR^8$, $C(O)NR^8R^9$, $NH_2$, $NHR^8$, $NR^8R^9$, $NHC(O)R^8$, or $NR^8C(O)R^9$;
$R^3$ and $R^4$ are the same or different and are selected from the group consisting of H, halogens, unsubstituted or substituted alkyl, OH, $OR^{10}$, $NH_2$, $NHR^{10}$, $NR^{10}R^{11}$, $NHC(O)R^{10}$, or $NR^{10}C(O)R^{11}$;
$R^5$, $R^6$, $R^7$, $R^8$, $R^9$, $R^{10}$, and $R^{11}$ are the same or different and are selected from the group consisting of unsubstituted alkyl and substituted alkyl;
$R^{12}$ is selected from the group consisting of H, unsubstituted alkyl, and substituted alkyl; and
Y is O or S;
provided that when n is 0, $R^2$ is selected from the group consisting of H, substituted alkyl other than $CH(OH)CH_3$, and unsubstituted alkyl;
further provided that when n is 2, $R^2$ is OH, $R^{12}$ is H, and both $R^3$ and $R^4$ are H, $R^1$ is not $CO_2CH_3$; and
further provided that when n is 2, $R^2$ is H, $R^{12}$ is H, and $R^3$ and $R^4$ are the same or different and are selected from the group consisting of H and $OCH_3$, $R^1$ is not $CO_2CH_3$;

or pharmaceutically acceptable salts thereof.

The present invention also provides a method of treating a subject addicted to an addictive substance. The method includes administering to the addicted subject an effective amount of a compound having the above formula, a compound having the above formula where n is 0 and $R^2$ is $CH(OH)CH_3$, a compound having the above formula where n is 2, $R^2$ is OH, $R^{12}$ is H, $R^3$ and $R^4$ are each H, and $R^1$ is $CO_2CH_3$, or a compound having the above formula where n is 2. $R^2$ is OH, $R^{12}$ is H, $R^3$ and $R^4$ are the same or different and are selected from the group consisting of H and $OCH_3$, and $R^1$ is $CO_2CH_3$.

The compounds of the present invention reduce both morphine and cocaine self administration in the addicted subject but do not affect other motivated behavior, such as bar pressing to obtain water. In addition, these compounds produce very little if any tremor, and no noticeable Purkinje cell degeneration.

DETAILED DESCRIPTION

Figure 1:
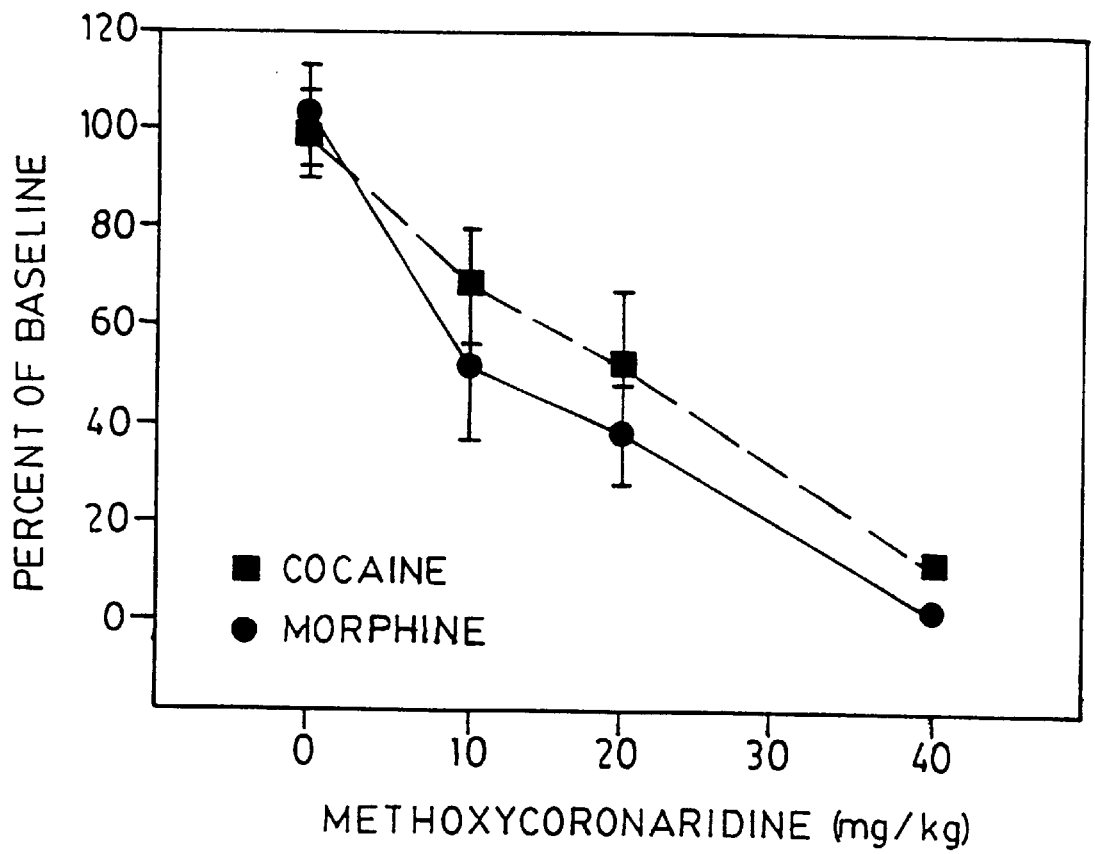
FIG. 1 is a plot of the acute effects of 18-methoxycoronaridine on morphine and cocaine self administration. Each data point is the mean (±S.E.) from 3–8 rats. Baseline was calculated as the average for the three sessions preceding drug or saline (0 mg/kg) administration. All doses had significant effects (ANOVA and t-tests, $P<0.05-0.001$).

The present invention relates to ibogamine congeners and to methods for treating addictive behavior using these congeners. One aspect of the present invention relates to a compound having the formula:

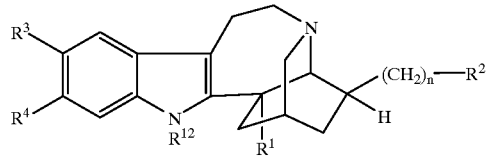

$R^1$ is selected from the group consisting of an alcohol, an ether, an ester, an amide, a hydrazide, a cyanide, or a ketone. Suitable alcohols include $CH_2OH$ and $CH(OH)R^5$, suitable ethers include those having the formulae $CH_2OR^5$, and suitable esters include those having the formulae $CO_2R^5$. Amides can be unsubstituted, such as $C(O)NH_2$, monosubstituted, such as, $C(O)NHR^5$, or disubstituted, such as $C(O)NR^5R^6$. Suitable hydrazides include unsubstituted hydrazides, having the formula $C(O)NHNH_2$, monosubstituted hydrazides, having the formulae $C(O)NHNHR^5$ or $C(O)NR^5NH_2$, disubstituted hydrazides, having the formulae $C(O)NHNR^5R^6$ or $C(O)NH^5NHR^6$, or trisubstituted hydrazides, having the formulae $C(O)NR^5NR^6R^7$. The hydrazides can also contain an amide functionality at the terminal nitrogen, such as hydrazides having the formulae $C(O)NHNH(C(O)R^5)$, $C(O)NHNR^5(C(O)R^6)$, $C(O)NR^5NH(C(O)R^6)$, or $C(O)NR^5NR^6(C(O)R^7)$. Suitable ketones are those where $R^1$ is $C(O)R^5$.

$R^5$, $R^6$, and $R^7$ can be either unsubstituted alkyl, such as, methyl, ethyl, n-propyl, iso-propyl, n-butyl, sec-butyl, tert-butyl, n-pentyl, sec-pentyl, and neo-pentyl, hexyl, heptyl, octyl, nonyl, decyl, dodecyl, dodecyl, and the like, or substituted with any of a number of known substituents, such as sulfo, carboxy, cyano, halogen (e.g., fluoro, chloro), hydroxy, alkenyl (e.g., allyl, 2-carboxy-allyl), alkoxy (e.g., methoxy, ethoxy), aryl (e.g, phenyl, p-sulfophenyl), aryloxy (e.g., phenyloxy), carboxylate (e.g., methoxycarbonyl, ethoxycarbonyl), acyloxy (e.g., acetyloxy), acyl (e.g., acetyl, propionyl), and others known to those skilled in the art. In addition, substituted alkyls include arylalkyls, such as 2-phenyleth-1-yl, 2-phenylprop-1-yl, benzyl, and arylalkyls bearing substitutents on the aromatic ring, such as 2-(5-chlorophenyl)prop-1-yl, N-piperidino, N-pyrrolidino, and N-morpholino. Each of $R^5$, $R^6$, and $R^7$ can be the same or different and the combination is selected primarily with consideration given to the substitution's effect on water-solubility and biological compatibility, although other factors, such as availability of starting materials and synthetic ease, may enter into the selection.

Suitable esters include ethyl ester, benzyl ester, dialkylaminoalkyl esters, and, preferably, methyl easter. Amides can be, for example, N-methylamide, N-ethylamide, N,N-dimethylamide, N,N-diethylamide, N-methyl-N-ethylamide, and peptides derived from amino acids and their esters or amides. $R^2$ can also be a hydrazide, such as N', N'-dimethylhydrazide, N',N''-dimethylhydrazide, or preferably, unsubstituted hydrazide.

The ibogamine skeleton can be unsubstituted at the C20 position (such as in the case of desethylcoronaridine), or it can be substituted at the C20 position with an alkyl or, preferably, a derivatized alkyl. The alkyl chain, represented in the above formula by $(CH_2)_n$, can have from zero to eight carbons, inclusive, such as methyl, ethyl, propyl, butyl, pentyl, hexyl, heptyl, and octyl, and is preferably ethyl. The alkyl chain is derivatized with $R^2$ at the terminal carbon of the alkyl chain (or, in the case where n is zero, at the C20 carbon). $R^2$ is selected from the group consisting of a hydrogen, a substituted or unsubstituted alkyl, a hydroxy, an ether, a thiol, a thioether, an amine, or an acid or thioacid derivative. In cases where n is zero, $R^2$ is preferably H or substituted or unsubstituted alkyl. Illustrative examples of suitable substituted or unsubstituted alkyls include those given for $R^5$, $R^6$, and $R^7$, above, Suitable ethers and thioethers have the formulae $OR^8$ and $SR^8$, respectively. Suitable amines include unsubstituted amines ($NH_2$), monosubstituted amines ($NHR^8$), or disubstituted amines ($NR^8R^9$). Acid or thioacid derivatives can have the formulae $OC(O)R^8$, $SC(O)R^8$, $C(O)NH_2$, $C(O)SR^8$, $C(O)SR^8$, $C(O)NHR^8$, $C(O)NR^8R^9$, $NHC(O)R^8$, or $NR^8C(O)R^9$. In each of the above, $R^8$ and $R^9$ can be the same or different and are selected from the group consisting of substituted or unsubstituted alkyl, examples of which are the same as those given for $R^5$, $R^6$, and $R^7$, above. As an illustration, suitable ethers and thioethers include methoxy, ethoxy, propoxy, butoxy, pentoxy, methoxyethoxymethyl ether ($OCH_2OCH_2CH_2OCH_3$), methylthio, ethylthio, dimethylaminoalkoxy, and sugar acetals, such as a glucoside. Suitable amine derivatives include methylamino, ethylamino, propylamino, butylamino, pentylamino, dimethylamino, diethylamino, dipropylamino, dibutylamino, methylethylamino, methylpropylamino, methylbutylamino, ethylpropylamino, ethylbutylamino, propylbutylamino, pyrrolidino, piperidino, and morpholino. Acid or thioacid derivatives can be, for example, $OC(O)CH_3$, $OC(O)CH_2CH_3$, $OC(O)(CH_2)_2CH_3$, $OC(O)(CH_2)_3$, $OC(O)(CH_2)_4CH_3$, $OC(O)(CH_2)_5CH_3$, $OC(O)(CH_2)_6CH_3$, $OC(O)(CH_2)_{10}CH_3$, $OC(O)(CH_2)_{12}CH_3$, $SC(O)(CH_2)_{20}CH_3$, $SC(O)CH_3$, $SC(O)CH_2CH_3$, $SC(O)(CH_2)_2CH_3$, $SC(O)(CH_2)_3CH_3$, $SC(O)(CH_2)_4CH_3$, $SC(O)(CH_2)_5CH_3$, $SC(O)(CH_2)_6CH_3$, $SC(O)(CH_2)_{10}CH_3$, $SC(O)(CH_2)_{12}CH_3$, $SC(O)(CH_2)_{20}CH_3$, $NHC(O)CH_3$, $NHC(O)CH_2CH_3$, $NHC(O)(CH_2)_2CH_3$, $NHC(O)(CH_2)_3$, $NHC(O)(CH_2)_{10}CH_3$, $NHC(O)(CH_2)_{12}CH_3$, $NHC(O)(CH_2)_{20}CH_3$, $N(CH_3)C(O)CH_3$, $N(CH_3)C(O)CH_2CH_3$, $N(CH_3)C(O)(CH_2)_2CH_3$, $N(CH_3)C(O)(CH_2)_3$, $N(CH_3)C(O)(CH_2)_{10}CH_3$, $N(CH_3)C(O)(CH_2)_{12}CH_3$, $N(CH_3)C(O)(CH_2)_{20}CH_3$, and esters and amides derived from amino acids and amino acid amides.

$R^3$ and $R^4$ can be the same or they can be different. Each can be selected from hydrogen, halide (such as fluoride, chloride, bromide, and iodide), alkyl, hydroxy, ether, or amine. The alkyl can be substituted or unsubstituted and is exemplified by the substituted or unsubstituted alkyls used to illustrate $R^5$, $R^6$, and $R^7$. Suitable ethers have the formulae $OR^{10}$ and suitable amines include unsubstituted amines ($NH_2$), monosubstituted amines ($NHR^{10}$), or disubstituted amines ($NR^{10}R^{11}$). In each of the above. $R^8$ and $R^9$ can be the same or different and are selected from the group consisting of substituted or unsubstituted alkyl, examples of which are the same as those given for $R^5$, $R^6$, and $R^7$, above. As an illustration $R^3$, $R^4$, or both $R^3$ and $R^4$ can be methoxy, ethoxy, propoxy, butoxy, pentoxy, methoxyethoxymethyl ether ($OCH_2OCH_2CH_2OCH_3$), methylamino, ethylamino, propylamino, butylamino, pentylamino, dimethylamino, diethylamino, dipropylamino, dibutylamino, methylethylamino, methylpropylamino, methylbutylamino, ethylpropylamino, ethylbutylamino, propylbutylamino, and arylalkyl, such as benzyl. In addition, the $R^3$ and $R^4$ substituents can be linked via an alkylene, such as methylene or ethylene to form a five- or six-membered ring, such as where $R^3$ and $R^4$, together, are —$OCH_2O$—, —$OCH_2CH_2O$—, —$NHCH_2O$—, —$NHCH_2CH_2O$—, —$NHCH_2NH$—, and —$NHCH_2CH_2NH$—, $R^{12}$ can be a hydrogen, a substituted alkyl, such as an arylalkyl, or an unsubstituted alkyl. Suitable unsubstituted and substituted alkyls include those used to exemplify $R^5$, $R^6$, and $R^7$, above.

Illustrative examples of compounds of the present invention are as follows:

18-hydroxycoronaridine;

18-hydroxyvoacangine;

18-hydroxyconopharyngine;

16-ethoxycarbonyl-18-hydroxyibogamine;

16-ethoxycarbonyl-18-hydroxyibogaine;

16-ethoxycarbonyl-18-hydroxyibogaline;

16-hydroxymethyl-18-hydroxyibogamine;

16-hydroxymethyl-18-hydroxyibogaine;

16-hydroxymethyl-18-hydroxyibogaline;

18-methoxycoronaridine;

18-methoxyvoacangine;

18-methoxyconopharyngine;

16-ethoxycarbonyl-18-methoxyibogamine;

16-ethoxycarbonyl-18-methoxyibogaine;

16-ethoxycarbonyl-18-methoxyibogaline;

16-hydroxymethyl-18-methoxyibogamine;

16-hydroxymethyl-18-methoxyibogaine;

16-hydroxymethyl-18-methoxyibogaline;

18-benzyloxycoronaridine;

18-benzyloxyvoacangine;

18-benzyloxyconopharyngine;

16-ethoxycarbonyl-18-benzyloxyibogamine;

16-ethoxycarbonyl-18-benzyloxyibogaine;

16-ethoxycarbonyl-18-benzyloxyibogaline;

18-hydroxycoronaridine laurate;

18-hydroxyvoacangine laurate;

18-hydroxyconopharyngine laurate;

16-ethoxycarbonyl-18-hydroxyibogamine laurate;

16-ethoxycarbonyl-18-hydroxyibogaine laurate;

16-ethoxycarbonyl-18-hydroxyibogaline laurate;

18-hydroxycoronaridine acetate;

18-hydroxyvoacangine acetate;

18-hydroxyconopharyngine acetate;

16-ethoxycarbonyl-18-hydroxyibogamine acetate;

16-ethoxycarbonyl-18-hydroxyibogaine acetate;

16-ethoxycarbonyl-18-hydroxyibogaline acetate;

18-hydroxycoronaridine methoxyethoxymethyl ether;

18-hydroxyvoacangine methoxyethoxymethyl ether;

18-hydroxyconopharyngine methoxyethoxymethyl ether;

16-ethoxycarbonyl-18-hydroxyibogamine methoxyethoxymethyl ether;

16-ethoxycarbonyl-18-hydroxyibogaine methoxyethoxymethyl ether;

16-ethoxycarbonyl-18-hydroxyibogaline methoxyethoxymethyl ether;

and pharmaceutically acceptable salts thereof.

Particularly preferred are compounds having the formulae:

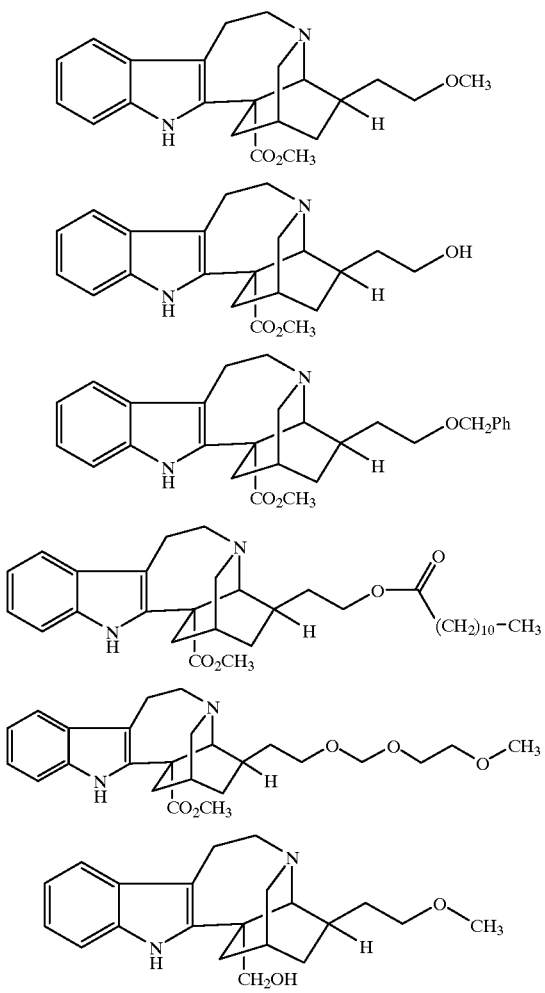

and pharmaceutically acceptable salts thereof.

As used herein, pharmaceutically acceptable salts are non-toxic salts which can be employed by those skilled in the art for in vivo use. Suitable pharmaceutically acceptable salts are the salts formed with inorganic acids, such as hydrochloric acid, sulfuric acid, nitric acid, and phosphoric acid, metal bicarbonates, such as sodium bicarbonate, monometal phosphates, such as monosodium phosphate, and dimetal phosphates, such as disodium phosphate. The salts can also be formed by reaction with organic acids, such as carboxylic acids or sulfonic acids. Suitable carboxylic acids include acetic, propionic, glycolic, lactic, pyruvic, malonic, succinic, fumaric, malic, tartaric, citric, cyclamic, ascorbic, maleic, hydroxymaleic, dihydroxymaleic, benzoic, phenylacetic, 4-aminobenzoic, anthranillic, cinnamic, salicyclic, 4-aminosalicyclic, 2-phenoxybenzoic, 2-acetoxybenzoic, and mandelic acid. Suitable sulfonic acids are, for example, methanesulfonic, ethanesulfonic, and β-hydroxyethane-sulfonic acid.

As will be recognized by those skilled in the art, the compounds of the present invention have four chiral carbon centers in the ibogamine skeleton. As used herein a "compound" of the present invention includes compounds having the aforementioned formulae without regard to the stereochemistry at these chiral centers. Accordingly, "compound" includes compounds which are racemic as well as to those which are optically pure with respect to the C20. In addition, the "compounds" of the present invention include those which are racemic and those which are optically pure with respect to the three bridgehead chiral carbons.

The compounds of the present invention can be synthesized using the methodology described in Bornmann [7] by reacting an appropriate 3-substituted-3-(1,3-dioxolan-2-yl) butanal having the formula:

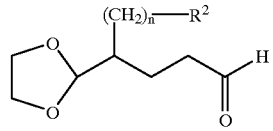

wherein
n is from 0 to 8 and
$R^2$ is H, unsubstituted alkyl, substituted alkyl, YH, $YR^8$, $YC(O)R^8$, $C(O)YR$, $C(O)NH_2$, $C(O)NHR^8$, $C(O)NR^8R^9$, $NR^8R^9$, $NHC(O)R^8$, $NR^8C(O)R^9$, $NHC(O)OR^8$, $NR^8C(O)OR^9$, $C(O)R^8$, or CN;
$R^8$ and $R^9$ are the same or different and are selected from the group consisting of unsubstituted or substituted alkyl; and
Y is O or S;
provided that when n is 0, $R^2$ is H, unsubstituted alkyl, or substituted alkyl
with an indoloazepine having the formula:

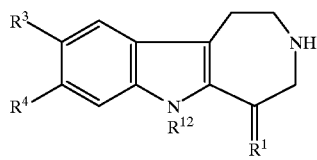

wherein
$R^1$ is $CO_2R^5$, $C(O)NH_2$, $C(O)NHR^5$, $C(O)NR^5R^6$, $C(O)NHNH(C(O)R^5)$, $C(O)NHN(C(O)R^5R^6)$, $C(O)NHNR^5R^6$, $C(O)NR^5NH(C(O)R^6)$, $C(O)NR^5NR^6(C(O)R^7)$, or $C(O)NR^5NR^6R^7$;
$R^3$ and $R^4$ are the same or different and are selected from the group consisting of H, halogens, unsubstituted or substituted alkyl, OH, $OR^{10}$, $NH(C(O)R^{10})$, $NR^{10}(C(O)R^{11})$, or $NR^{10}R^{11}$;
$R^5$, $R^6$, $R^7$, $R^{10}$, and $R^{11}$ are the same or different and are selected from the group consisting of unsubstituted or substituted alkyl; and
and $R^{12}$ is selected from the group consisting of H unsubstituted alkyl, and substituted alkyl
under conditions effective to form a condensation produce having the formula:

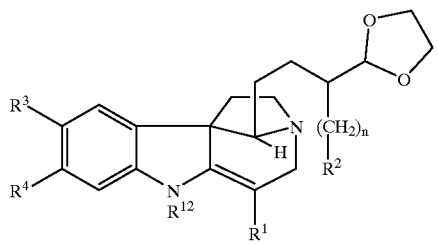

Typically, equimolar amounts of the two reactants are dissolved in an organic solvent and maintained at room temperature for ½ to 72 hours, preferably for 16 hours. Suitable solvents include alcohol solvents, such as methanol, ethanol, isopropanol, and n-butanol; ester-containing solvents, such as ethyl acetate and isopropyl acetate; ether solvents, such as tetrahydrofuran, diglyme, and dioxane; chlorinate hydrocarbons, such as methylene chloride, chloroform, and carbon tetrachloride; aromatic hydrocarbons, such as benzene, toluene, and xylene; acetonitrile; pyridine; and dimethylformamide. Preferably, a solvent is chosen in which both reactants are substantially soluble. Methanol is particularly preferred.

After reaction is complete, the condensation product is treated in a suitable solvent with an equivalent amount of an appropriate arylalkyl containing a good leaving group, such as an arylalkyl tosylate, an arylalkyl mesylate, or an arylalkyl halide, preferably benzyl bromide, for 0.5 to 72 hours, preferably 16 hours, at 50° C. to 120° C., preferably at the reflux temperature of the solvent. Suitable solvents include lower alkanes, such as pentane, hexane, or petroleum ether; aromatic hydrocarbon solvents, such as benzene, toluene, and xylene; alcohols, such as methanol, ethanol, isopropanol, and n-butanol; and ether solvents, such as diethyl ether, diglyme, or tetrahydrofuran.

Treatment of the product, with an organic-soluble Lewis base, preferably triethylamine, produces a transient enamine acrylate having the formula:

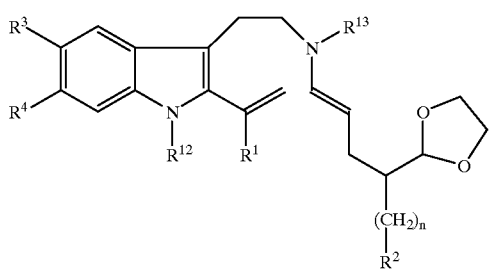

Typical solvents for the base treatment include alcohol solvents, such as methanol, ethanol, isopropanol, and n-butanol; ketone solvents, such as acetone, methyl ethyl ketone, and cyclopentanone; ester-containing solvents, such as ethyl acetate and isopropyl acetate; ether solvents, such as tetrahydrofuran, diglyme, and dioxane; chlorinated hydrocarbons, such as methylene chloride, chloroform, and carbon tetrachloride; acetonitrile; pyridine; and dimethylformamide. Preferably, a solvent is chosen in which both reactants are substantially soluble. Methanol is particularly preferred. Base treatment can be conducted at any temperature from room temperature to the boiling point of the solvent, but is advantageously effected with slight heating preferably from 50° C. to 70° C. for from 1 to 10 hours.

The transient enamine acrylate spontaneously cyclizes to produce a versatiline derivative having the formula:

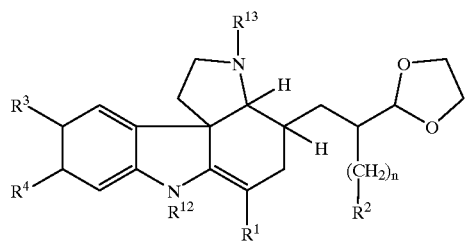

Alternatively, the versatiline derivative can be prepared in accordance with the method described by Kuehne [8].

Briefly, the 3-substituted-3-(1,3-dioxolan-2-yl)butanal is treated with an N-arylalkyl derivative having the formula:

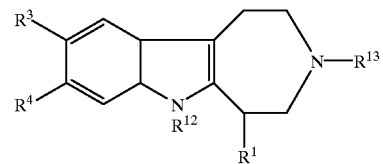

where $R^{13}$ is an aryllkyl, such as benzyl. Suitable solvents for the reaction include aromatic solvents, such as benzene, toluene, and xylene; ester-containing solvents, such as ethyl acetate and isopropyl acetate; ether solvents, such as tetrahydrofuran, diglyme, and dioxane; chlorinated hydrocarbons, such as methylene chloride, chloroform, and carbon tetrachloride; acetonitrile; pyridine; and dimethylformamide. Toluene is particularly preferred. The reaction is typically conducted at a temperature from 100° C. to 120° C. preferably at reflux.

Irrespective of the route used in its preparation, the versatiline derivative is then converted to a cleavamine having the formula:

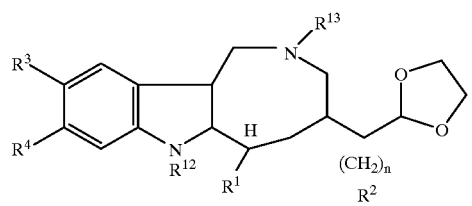

by reduction with, for example, sodium borohydride in an acidic solvent, preferably acetic acid. The reduction is effected by heating, preferably to a temperature between 80° C. and 110° C., more preferably between 85° C. and 95° C.

Reduction, preferably catalytic reduction using $H_2$ over palladium/carbon catalyst, followed by treatment with acidic alcohol, preferably with hydrochloric acid in methanol, followed by addition of a base, such as ammonium hydroxide, yields an enamine having the formula:

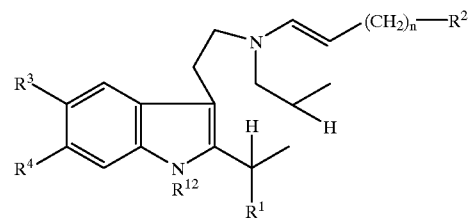

The enamine is then heated, preferably at between 80° C. and 120° C. for 4 to 12 hours in a suitable solvent, to produce a compound of the present invention having the formula 1:

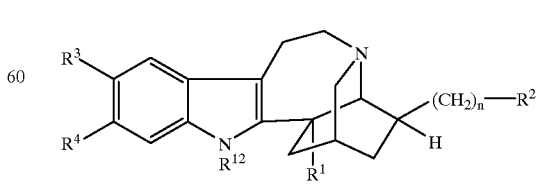

1

Suitable solvents include aromatic solvents, such as benzene, toluene, and xylene; ether solvents, such as tetrahydrofuran, diglyme, and dioxane; chlorinated hydrocarbons, such as methylene chloride, chloroform, and carbon tetrachloride; acetonitrile; pyridine; and dimethylformamide. Toluene is particularly preferred. Alternatively, the compound of the present invention can be prepared by storing the enamine under vacuum or in an inert atmosphere, such as under argon or nitrogen, for at least 12 hours, preferably 4 days to 6 days.

As an alternative to using a 3-substituted-(1,3-dioxolan)-2-yl)butanal, where $R^2$ is hydroxy, compounds of the present invention bearing a C18 hydroxyalkyl moiety ($1(R^2=OH)$) can also be prepared by reduction of the corresponding C18 alkyl ester (such as, $1(R^2=COOR^5)$), for example, with a half-molar equivalent of lithium aluminum hydride or with diisobutylaluminum hydride. Compounds bearing the alkoxyalkyl moiety ($1(R^2=OR^5)$) can likewise be prepared from the corresponding esters ($1(R^2=COOR^5)$), such as by reduction with $LiAlH_4/AlCl_3$. In a similar manner, it can be advantageous to prepare compounds of the present invention having basic amines (such as $1(R^2=NH_2$ or $R^2=NHR^8)$) from the corresponding amides (such as $1(R^2=NHC(O)R^8$ or $R^2=NR^8C(O)R^9)$) by hyrdrolysis with aqueous acid rather that by starting with amine-containing 3-substituted-(1,3-dioxolan)-2-yl)butanal. The amide to amine conversion can also be effected by conventional procedures, such as with diisobutylaluminum hydride in an ether, preferably tetrahydrofuran ("THF") to give a substituted amine. Again, this alternative method is particularly advantageous when n is less than three.

Compounds having C16 hydroxy or alkoxymethyl substitutents are prepared by reduction of the corresponding C16 ester, such as with $LiAlH_4/THF$ to the C16 hydroxymethyl or with $LiAlH_4/AlCl_3$ to the C16 alkoxymethyl. Reduction of C16 amides with $LiAlH_4$ would provide C16 amines. C16 hydrazides containing basic nitrogens (such as $1(R^1=C(O)NHNH_2, C(O)NHNR^5, C(O)NR^5NH_2,$ or $C(O)NR^5NHR^6)$) can be prepared from the corresponding hydrazide carbamates, typically t-butyl carbamate, by hydrolysis with acids.

Subsequent to preparation, the compound of the present invention can optionally be purified by recrystallization, solvent extraction using, for example, a Soxhlet extraction apparatus, chromatography, such as HPLC or conventional column chromatography, or other conventional purification methods. In addition, prior to, subsequent to, or as an aid in isolation, the compounds of the present invention can be converted to the acid addition salt, such as by contacting a solution of the compound with an appropriate acid.

Preparation of the 3-substituted-(1,3-dioxolan-2-yl) butanal starting materials, is achieved by conventional methods. Typically these reactants are prepared by oxidation of a 2-substituted-4-hydroxybutyric ester. The latter can be obtained by alkylation of a allylmalonic ester with an alkyl halide and a base (e.g. sodium alkoxide) followed by decarboalkoxylation with LiCl, hydroboration with diborane or with borane dimethylsulfide complex, and oxidation with hydrogen peroxide and sodium hydroxide. Oxidation of the 4-hydroxy-2-substituted butanoic ester is achieved with dimethyl sulfoxide and oxalyl chloride. The resulting aldehyde is protected, preferably as its acetal with ethylene glycol. Reduction of the ester function, such as with $LiAlH_4$, is followed by oxidation of the resultant alcohol with dimethylsulfoxide and oxalyl chloride.

The indoloazepine starting material, with which the butanal is reacted, is typically prepared by methods which have been well-developed in the art, such as those described in references [9–13]. Briefly, the indoloazepine starting material can be prepared by condensation of tryptamine with methyl 3-chloropyruvate. The resulting carboline is heated in pyridine to provide an unsaturated indoloazepine (vinylogous urethane). The latter is reduced with sodium cyanoborohydride.

When using the alternative route to the preparation of versatiline derivatives, the appropriately substituted $N^b$-benzylindoloazepine is prepared by alkylation of the above $N^b$-H indoloazepine with benzyl bromide and sodium carbonate. Alternatively, indoloazepines with substituents on the aromatic ring can be made by Fischer Indole synthesis from substituted phenylhydrazines and N-benzyl-4-piperidones, followed by reaction with t-butyl hypochlorite and thallium dimethyl malonate, and, then, with lithium chloride.

The compounds of the present invention are useful in treating subjects, such as mammals and including rats and humans, exhibiting addictive behavior, by administering the compounds to such subjects in an effective amount. The compounds of the present invention may be administered alone or in combination with suitable pharmaceutical carriers or diluents. The diluent or carrier ingredients should be selected so that they do not diminish the therapeutic effects of the compounds of the present invention.

The compounds herein may be made up in any suitable form appropriate for the desired use; e.g., oral, parenteral, or topical administration. Examples of parenteral administration are intraventricular, intracerebral, intramuscular, intravenous, intraperitoneal, rectal, and subcutaneous administration.

Suitable dosage forms for oral use include tablets, dispersible powders, granules, capsules, suspensions, syrups, and elixirs. Inert diluents and carriers for tablets include, for example, calcium carbonate, sodium carbonate, lactose, and talc. Tablets may also contain granulating and disintegrating agents such as starch and alginic acid, binding agents such as starch, gelatin, and acacia, and lubricating agents such as magnesium stearate, stearic acid, and talc. Tablets may be uncoated or may be coated by known techniques to delay disintegration and absorption. Inert diluents and carriers which may be used in capsules include, for example, calcium carbonate, calcium phosphate, and kaolin. Suspensions, syrups, and elixirs may contain conventional excipients, for example, methyl cellulose, tragacanth, sodium alginate; wetting agents, such as lecithin and polyoxyethylene stearate; and preservatives, e.g., ethyl-p-hydroxybenzoate.

Dosage forms suitable for parenteral administration include solutions, suspensions, dispersions, emulsions, and the like. They may also be manufactured in the form of sterile solid compositions which can be dissolved or suspended in sterile injectable medium immediately before use. They may contain suspending or dispersing agents known in the art.

One aspect of the present invention is directed to therapeutically treating a subject suffering from an addiction to an addictive substance. In particular, the compounds of the present invention are useful where the addictive substance is a barbituate; an opiate, such as morphine, codeine, heroin, levorphanol, meperidine, methadone, propoxyphene, acetylmethadol (LAAM), pentazocine, butorphanol, nalbuphine, buprenorphine, dezocine, fentanyl, and combinations of these opiates; a stimulant, such as d-amphetamine, 1-amphetamine, dl-amphetamine, methamphetamine, benzphetamine, phentermine, diethylpropion, phenmetrazine, phendimetrazine, chlorphentermine, clortermine, mazindol, phenylpropanolamine, cocaine, methylphenidate, nicotine, cathinone (khat plant), and combinations of these stimulants; a depressant, such as meprobamate, chlordiazepoxide, diazepam, oxazepam, lorazepam, flurazepam, prazepam, chlorazepate, alprazolam, triazolam, temazepam, halazepam, quadazepam, midazolam, estazolam, ethanol, pentobarbital, phenobarbital, secobarbital, amobarbital, and combinations of these depressants; or combinations of these addictive substances. The subject can be addicted to one of these addictive substances or to a plurality of these addictive substances.

Treatment comprises administering to the mammal an effective amount of a compound having the formula:

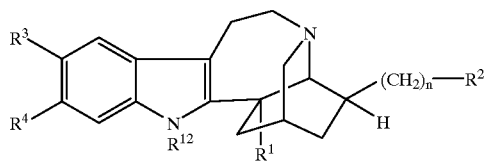

wherein
n is from 0 to 8;
$R^1$ is $CH_2OH$, $CH(OH)R^5$, $CH_2OR^5$, $CO_2R^5$, $C(O)NH_2$, $C(O)NHR^5$, $C(O)NR^5R^6$, $C(O)NHNH_2$, $C(O)NHNHR^5$, $C(O)NHNR^5R^6$, $C(O)NR^5NH_2$, $C(O)NR^5NHR^6$, $C(O)NR^5NR^6R^7$, $C(O)NHNH(C(O)R^5)$, $C(O)NHNR^5(C(O)R^6)$, $C(O)NR^5NH(C(O)R^6)$, $C(O)NR^5NR^6(C(O)R^7)$, CN, or $C(O)R^5$;
$R^2$ is H, unsubstituted or substituted alkyl, YH, $YR^8$, $YC(O)R^8$, $C(O)YR^8$, $C(O)NH_2$, $C(O)NHR^8$, $C(O)NR^8R^9$, $NH_2$, $NHR^8$, $NR^8R^9$, $NHC(O)R^8$, or $NR^8C(O)R^9$;
$R^3$ and $R^4$ are the same or different and are selected from the group consisting of H, halogens, unsubstituted or substituted alkyl, OH, $OR^{10}$, $NH_2$, $NHR^{10}$, $NR^{10}R^{11}$, $NHC(O)R^{10}$, or $NR^{10}C(O)R^{11}$;

$R^5$, $R^6$, $R^7$, $R^8$, $R^9$, $R^{10}$, and $R^{11}$ are the same or different and are selected from the group consisting of unsubstituted alkyl and substituted alkyl;
$R^{12}$ is selected from the group consisting H, unsubstituted alkyl, and substituted alkyl; and
Y is O or S;
provided that when n is O, $R^2$ is selected from the group consisting of H, substituted alkyl, and unsubstituted alkyl;

or a pharmaceutically acceptable salt thereof.

It will be appreciated that the actual preferred amount of compound of the present invention used will vary according to the particular compound, the particular composition formulated, and the mode of application. Many factors that modify the action will be taken into account by those skilled in the art; e.g., body weight, sex, diet, time of administration, route of administration, rate of excretion, condition of the host, drug combinations, reaction sensitivities and severities and severity of addiction. Administration can be carried out continuously or periodically within the maximum tolerated dose. Optimal application rates for a given set of conditions can be ascertained by those skilled in the art using conventional dosage administration tests in view of the above guidelines. Preferably the compound is administered in a dose from about 1.0 to about 80 mg/kg of the subject's mass.

The present invention is further illustrated by the following examples.

EXAMPLES

Ibogamine congeners were synthesized as described in detail below with reference to the following reaction scheme:

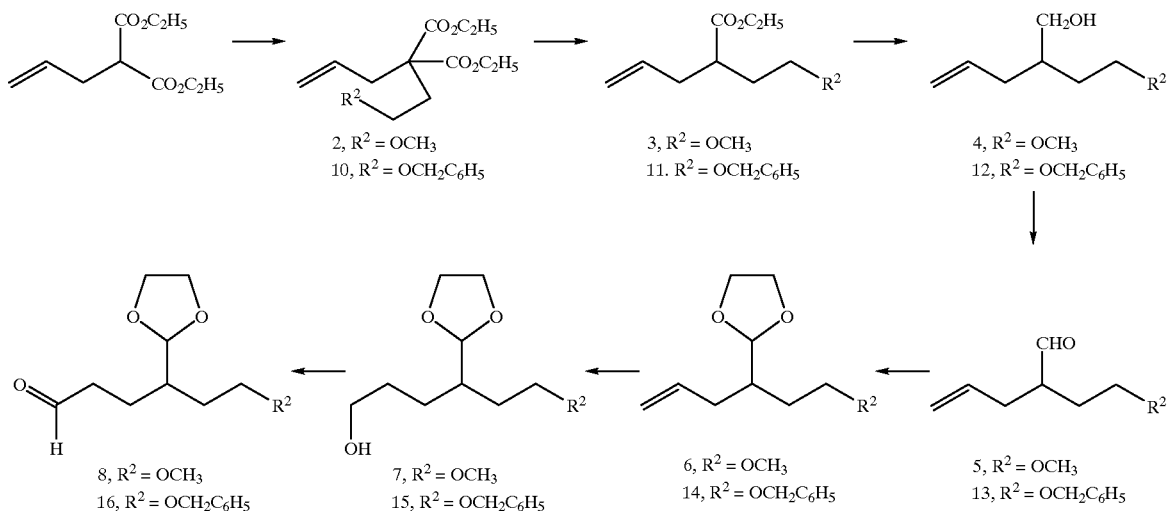

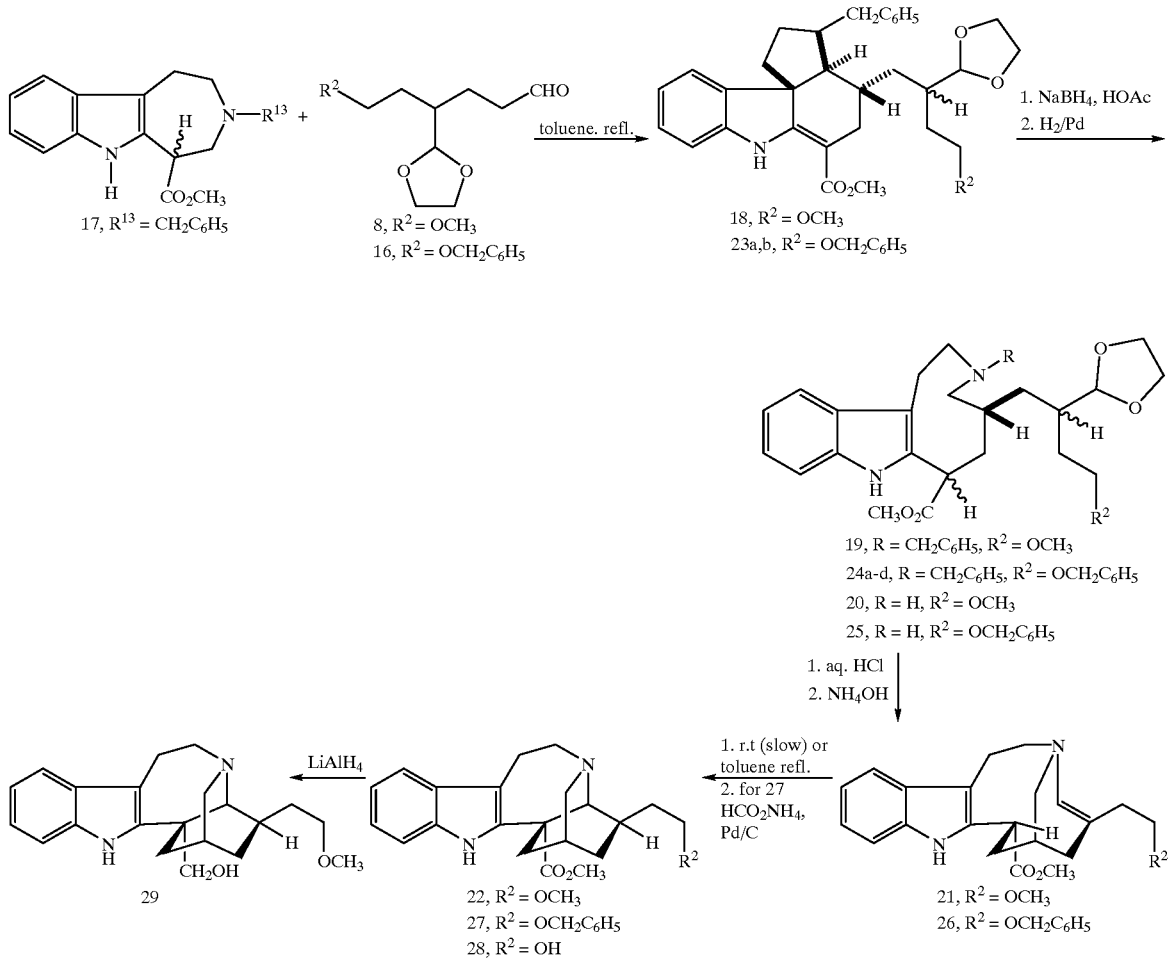

Example 1

Diethyl 2-(2-methoxyethyl)-2-allylmalonate (2).

Metallic sodium (15 g, 230 mmol) was dissolved in dry ethanol (250 mL) with cooling in an ice bath, under nitrogen, and diethyl allylmalonate (Lancaster Synthesis, Windham, Mass.) (105 g, 525 mmol) in absolute ethanol (50 mL) was added dropwise under nitrogen. The mixture was stirred at room temperature for 1 h. and 2-bromoethyl methyl ether (87.57 g, 630 mmol) in absolute ethanol (50 mL) was then added dropwise. The mixture was heated at reflux for 3 h and then cooled to room temperature. The precipitate solid was filtered and washed with ethanol (2×100 mL). The residue obtained upon concentration of the filtrate was diluted with water (1 L). The mixture was extracted with ether (2×150 mL), dried over $MgSO_4$ and concentrated to give the diester ether 2 (118 g, 87%) as a viscous liquid. IR (KBr) $\upsilon_{max}$ 3069, 2971, 2927, 1734, 1640, 1459, 1443, 1382, 1361, 1284, 1223, 1196, 1119, 1077, 1031, 922, 856 cm$^{-1}$; $^1$HNMR ($CDCl_3$) δ1.24 t, J=7.0 Hz, 6 H), 2.17 (t, J=6.4 Hz, 2 H), 2.68 (d, J=7.1 Hz, 2 H), 3.2 (s, 3 H), 3.41 (t, J=6.5 Hz, 2 H), 4.17 (dis q, 4 H), 5.04–5.12 (m, 2 H), 5.63–5.79 (m, 1 H); $^{13}$CNMR ($CDCl_3$) δ13.98, 32.05, 37.31, 55.08, 58.52, 61.13, 68.34, 118.93, 132.49, 170.17; mass spectrum (EI), m/z (rel itensity) 259 (M$^+$+1.16), 227 (20), 213 (19), 200 (37), 185 (13), 167 (17), 154 (25), 153 (65), 139 (38), 125 (25), 108 (100), 81 (30), 79 (31), 67 (23), 59 (23), 53 (23).

Example 2

Ethyl 2-(2-methoxyethyl)-pent-4-enoate (3)

A mixture of diester 2 (40 g, 155 mmol), prepared according to Example 1, and lithium chloride (13 g, 300 mmol) in DMSO (100 mL). DMF (20 mL), and water (2 mL) was heated to 170° C. for 6 h and cooled to room temperature. The mixture was poured into water (250 mL), extracted with $CH_2Cl_2$ (3×100 mL), and dried over $MgSO_4$. The solvent was removed under reduced pressure to afford the monoester ether 3 (25.2 g, 87%); IR (KBr) $\upsilon_{max}$ 3079, 2974, 2921, 2869, 1732, 1640, 1461, 1443, 1470, 1374, 1177, 1121, 1029, 990, 916, 855 cm$^{-1}$; $^1$HNMR ($CDCl_3$) δ1.25 (t, J=7.05 Hz, 3H), 1.65–1.75 (m, 1H), 1.85–1.95 (m, 1H), 2.20–2.40 (m, 2H), 2.50–2.60 (m, 1H), 3.30 (s, 3H), 3.35–3.45 (m, 2H), 4.13 (q, J=7.05, 2H), 5.00–5.07 (dd, J=10.2, 25 Hz, 2H), 5.71–5.74 (m, 1H); $^{13}$CNMR ($CDCl_3$) δ14.21, 31.44, 36.45, 42.12, 58.48, 60.12, 70.37, 70.38, 116.79, 135.19, 175.19; mass spectrum (EI), m/Z (rel intensity) 223 (11), 200 (19), 185 (M-1, 4.5), 154 (19), 153 (46), 143 (33), 128 (33), 121 (37), 120 (34), 112 (22), 108 (88), 95 (28), 82 (41), 81 (98), 79 (94), 59 (38), 57 (71), 55 (100), 54 (38), 53 (59),

Example 3

2-(2-Methoxyethyl)-pent-4-en-1-ol (4)

A 1M solution of lithium aluminum hydride (135 mL), 134 mmol) was added via cannula to a stirred solution of the ester 3 (25 g, 134 mmol), prepared according to Example 2, in dry ether (200 mL). The mixture was stirred for 2 h at room temperature under nitrogen and cooled to 0° C., and water (10 mL) was added dropwise, with stirring, followed by dropwise addition of 15% NaOH (10 mL) and water (30 mL) at 0° C. to produce a white precipitate. The precipitate was filtered, and washed with ether (2×50 mL). The filtrate was dried over MgSO$_4$, filtered, and concentrated to give the alcohol 4 (16.5 g, 85.4%). IR (KBr) $\upsilon_{max}$ 34,10, 3071, 2930, 2860, 1641, 1442, 1384, 1185, 1109, 1043, 993, 911 cm$^{-1}$; $^1$HNMR (CDCl$_3$) δ1.61–1.75 (m, 3 H), 2.02–2.30 (m, 2 H), 3.35 (s, 3 H), 3.36–3.60 (m, 4 H), 5.01–5.06 (m, 2 H), 5.77–5.79 (m, 1 H); $^{13}$CNMR (CDCl$_3$): δ31.33, 35.95, 38.56, 58.20, 65.17, 70.98, 116.07, 136.59; mass spectrum (EI), m/z (rel intensity) 145 (7), 144 (M$^+$, 3), 143 (23), 126 (15), 113 (20), 111 (42), 102 (17), 95 (27), 94 (57), 93 (31), 83 (49), 82 (41), 81 (61), 79 (100), 71 (70), 70 (42), 69 (38), 67 (65), 58 (46), 57 (34), 55 (75), 54 (48), 53 (34).

Example 4

2-(2-Methoxyethyl)-4-penten-1-al (5)

Dry dimethylsulfoxide (18.4 mL, 260 mmol) in dry CH$_2$Cl$_2$ (30 mL) was added dropwise to a stirred solution of 2M (COCl)$_2$ (65 mL, 130 mmol) at −78° C. during 15 min under nitrogen. The alcohol 4 (15 g, 104 mmol), prepared according to Example 3, in dry dichloromethane (50 mL) was then added during 10 min. resulting in a slightly cloudy solution, which was stirred for 30 min at −78° C. A solution of triethyl amine (75 mL, 520 mmol) in dichloromethane (50 mL) was then added dropwise during 15 min. The mixture was then stirred for 1h at room temperature, and the reaction was quenched by adding water (25 mL), with rapid stirring. The resulting slurry was immediately poured into ether (300 mL) and washed with 20% KHSO$_4$ (2×200 mL). The layers were separated, and the aqueous layer was extracted with ether (2×100 mL). The combined organic layers were washed with brine solution (2×100 mL), dried over MgSO$_4$, filtered, and concentrated to afford the crude aldehyde 5 (12.4 g, 84%) as an oil, which was used in the following condensation with ethylene glycol, IR (KBr) $\upsilon_{max}$ 2951, 2921, 2863, 1720, 1638, 1456, 1379, 1255, 1121, 1033, 997, 909 cm$^{-1}$; $^1$HNMR (CDCl$_3$) δ1.73–1.77 (m, 1 H), 1.92–1.96 (m, 1 H), 2.23–2.27 (m, 1 H), 2.42–2.46 (m, 1 H), 2.50–2.52 (m, 1 H), 3.29 (s, 3 H), 3.39–3.43 (m, 2 H), 5.05–5.10 (m, 2 H), 5.72–5.77 (m, 1 H), 9.64 (s, 1 H); $^{13}$CNMR (CDCl$_3$) δ28.65, 33.04, 48.57, 58.57, 70.00, 117.40, 134.85; mass spectrum (EI), m/z (rel intensity) 167 (23), 157 (17), 149 (100), 143 (16), 142 (4, M$^+$), 141 (12), 129 (28), 127 (64), 112 (22), 111 (26), 109 (14), 100 (16), 97 (23), 95 (31), 93 (22), 87 (24), 85 (36), 84 (53), 83 (45), 82 (21), 81 (49), 79 (27), 71 (70), 70 (26), 69 (51), 67 (55), 59 (49), 57 (80), 55 (87), 53 (31).

Example 5

4-(1,3-Dioxolan-2yl)-6-methoxy-1-hexane (6)

A stirred solution of crude aldehyde 5 (12.4 g, 87.20 mmol), prepared according to Example 4, ethylene glycol (8.1 g, 130 mmol), p-toluene sulfonic acid monohydrate (1 g) in dry benzene (200 mL) contained in a 500 mL round-bottom flask fitted with a Dean Stark trap was heated at reflux for 12 hrs. The mixture was cooled to room temperature, the benzene layer was separated, and the aqueous layer was extracted with ether (2×100 ml). Combined organic layers were dried over MgSO$_4$ and filtered. The residue obtained on concentration was purified by flash column chromatography on silica gel using ether/hexane (1:1) as eluant to give 6 (14.5 g, 89%) as an oil. IR (KBr) $\upsilon_{max}$ 2981, 2934, 2832, 1637, 1457, 1388, 1119, 1036, 988, 947, 906 cm$^{-1}$; $^1$HNMR (CDCl$_3$) δ1.57–1.85 (m, 3H), 2.09–2.45 (m, 2H), 3.31 (s, 3H), 3.44 (t, J=6.4 Hz, 2H), 3.83–3.94 (m, 4H), 4.81 (s, 1H, 4.99–5.07 (m, 2H), 5.75–5.90 (m, 1H); $^{13}$CNMR (CDCl$_3$) δ28.42, 33.83, 58.29, 64.82, 64.92, 70.87, 106.01, 116.07, 136.66: mass spectrum (EI), m/Z (rel intensity) 186 (M$^+$, 9), 155 (11), 141 (9), 127 (10), 111(11), 99 (30), 84 (32), 79 (29), 73 (100), 55 (7).

Example 6

4-(1,3-Dioxolan-2-yl)-6-methoxyhexan-1-ol (7)

A 1M solution of borane-methyl sulfide complex in dichloromethane (18 mL, 18 mmol) was added dropwise to a stirred solution of the olefinic acetal 6 (10 g, 53.7 mmol), prepared according to Example 5, in hexane (40 mL) at 0° C. The mixture was stirred for 3 h at room temperature and then cooled to 0° C., and then absolute ethanol (10 mL) was added dropwise, followed by 15% NaOH (10 mL) and 30% H$_2$O$_2$ (10 mL). The reaction mixture was heated at reflux for 1 h, cooled to room temperature, and poured into water (200 mL). The organic layer was separated, and the aqueous layer was extracted with ether (3×50 mL). The organic layers were combined, dried over MgSO$_4$, and concentrated under reduced pressure. The crude product was chromatographed on a silica gel column, eluting with 2% methanol in ether, to give the alcohol 7 (6.1 g, 56%) as a viscous liquid. IR (KBr) $\upsilon_{max}$ 3434, 2929, 2808, 1646, 1451, 1403, 1111, 953 cm$^{-1}$; $^1$HNMR (CDCl$_3$) δ1.30–1.85 (m, 7 H), 3.30 (s, 3 H), 3.43–3.50 (m, 2 H), 3.61 (t, J=6.3 Hz, 2 H), 3.83–4.00 (m, 4 H), 4.79 (d, J=3.7 Hz, 1 H); $^{13}$CNMR (CDCl$_3$) δ25.44, 29.04, 30.15, 58.33, 62.66, 64.78, 64.84, 70.98, 106.45, 33.83, 58.29, 64.82, 64.92, 70.87, 106.01: mass spectrum (EI), m/z (rel intensity) 159 (M$^+$−45, 6.4), 143 (29), 127 (95), 111 (35), 73 (100), 67 (7), 55 (83).

Example 7

4-(1,3-Dioxolan-2-yl)-6-methoxyhexanal (8).

The alcohol 7 (6 g, 29.37 mmol), prepared according to Example 6, was oxidized using 2M (COCl)$_2$ (18 mL, 36 mmol), dry DMSO (5.1 mL, 72 mmol) and triethyl amine (20.7 mL, 144 mmol) analogous to the oxidation of the alcohol 4, as described in example 4. Similar work up as for 5 gave the aldehyde 8 (4.8 g, 81%) as a colorless oil. IR (KBr) $\upsilon_{max}$ 2939, 2880, 2735, 1719, 1451, 1391, 1111, 1038, 947 cm$^{-1}$: $^1$HNMR (CDCl$_3$) δ1.45–2.85 (m, 5 H), 2.54 (t, J=6.8 Hz, 2 H), 3.31 (s, 3 H), 3.43–3.46 (m, 2 H), 3.83–3.95 (m, 4 H), 2.54 (t, J=6.8 Hz, 2 H), 3.31 (s, 3 H), 3.43–3.46 (m, 2 H), 3.83–3.95 (M, 4 H), 4.77 (d, J=3.3 Hz, 1 H), 9.76 (t, J=1.5 Hz, 1 H); $^{13}$CNMR (CDCl$_3$) δ21.51, 29.23, 37.99, 41.72, 58.42, 64.81, 64.88, 70.66, 106.26, 202.39: mass spectrum (EI), m/z (rel intensity) 210 (33), 202 (M$^+$, 3), 201 (15), 157 (19), 144 (27), 143 (38), 141 (19), 127 (17), 126 (1), 111 (30), 109 (12), 100 (4), 99 (11), 73 (100), 59 (10), 57 (8), 55 (12), 54 (5).

Example 8

2-Benzyloxy bromide (9)

To a suspension of triphenylphosphine (69 g, 263 mmol) in anhydrous acetonitrile (200 mL) was added bromine (13.6 mL, 263 mmol), dropwise, with stirring at 0° C. over 15 min, and then 2-benzyloxyethanol (40 g, 263 mmol) (Aldrich Chemical Co., St. Louis, Mo.) in dry acetonitrile (25 mL) was added dropwise at 0° C. over 30 min. The yellow colored solution was stirred for an additional 30 min at 0° C., and the solvent was evaporated under reduced pressure. The residue was suspended in ether (200 mL), and the precipitated solid was filtered and washed with ether (3×100 mL). The filtrate was concentrated, and the residue was chromatographed on a silica gel column, eluting with ether/hexane (1:4) to give 9 (43 g, 77%) as a pale yellow liquid. IR (KBr) $v_{max}$ 3087, 3063, 3030, 2964, 2859, 1495, 1453, 1422, 1360, 1276, 1205, 1110, 1040, 1028, 738, 698, 672 $cm^{-1}$; $^{1}$HNMR (CDCl$_3$) δ3.47 (t, J=6 Hz, 2 H), 3.77 (t, J=6 Hz, 2 H), 4.57 (s, 2 H), 7.28–7.35 (m, 5 H); $^{13}$CNMR (CDCl$_3$) δ30.39, 69.99, 73.14, 127.72, 127.84, 128.47, 137.76.

Example 9

Diethyl 2-(2-Benzyloxyethyl)-allylmalonate (10)

Sodium (5.3 g, 230 mmol) was dissolved in dry ethanol with cooling in an ice bath and diethyl allylmalonate (36.84 g, 184 mmol) in absolute ethanol (50 mL) was added dropwise, under nitrogen. The mixture was stirred at room temperature for 1 h, and the bromide 9 (39.62 g, 184.2 mmol), prepared according to Example 8, in absolute ethanol (50 mL) was added dropwise. The mixture was heated to 60° C. for 3 h and cooled to room temperature. Precipitated solid was filtered and washed with ethanol (2×50 mL). The residue obtained upon concentration of the filtrate was diluted with water (500 mL). The mixture was extracted with ether (3×100 mL), dried over MgSO$_4$, and concentrated to give a viscous liquid (54 g). $^{1}$HNMR of this product showed a 3:1 ratio of 10 and benzyloxy-2-ethoxy ethanol. The mixture of products was inseparable by chromatography and hence the mixture was directly subjected to decarboethoxylation. IR (KBr) $v_{max}$ 3077, 2989, 2874, 1741, 1456, 1347, 1279, 1220, 1201, 1106, 1030, 926, 858, 741, 702, $cm^{-1}$; $^{1}$HNMR (CDCl$_3$) δ 1.19 (t, J=7.4 Hz, 6 H), 2.24 (t, J=6.5 Hz 2 H), 2.69 (d, J=7.4 Hz, 2 H), 3.51 (t, J=6.5 Hz, 2 H), 4.13 (q, J=7.4 Hz, 4 H), 4.43 (s, 2 H), 5.04–5.07 (m, 2 H), 5.60–5.70 (m, 1 H), 7.20–7.40 (m, 5 H); $^{13}$CNMR (CDCl$_3$) δ 13.88, 32.01, 37.08, 55.57, 61.01, 65.78, 72.83, 118.78, 127.31, 127.46, 128.06, 132.40, 138.10, 170.82; mass spectrum (EI), m/z (rel intensity) 335 (1.2), 334 (M$^+$,0.75), 249 (9.5),2.77 (15), 203 (22), 200 (60), 180 (40), 143 (17), 134 (22), 127 (22), 125 (15), 109 (25), 108 (70), 107 (90), 105 (55), 91 (100), 89 (15), 65 (14).

EXAMPLE 10

Ethyl 2-(2-Benzyloxyethyl)-pent-4-enoate (11)

A mixture of crude diester 10 (54 g), prepared according to Example 9, and lithium chloride (10.1 g, 234.67 mmol) in DMSO (78 mL), DMF (15 mL), and water (1.5 mL) was heated at 170° C. for 6 h and cooled to room temperature. The mixture was poured into water (250 mL) and extracted with CH$_2$Cl$_2$(3×100 mL), and the extract was dried over MgSO$_4$. The solvent was removed under reduced pressure to afford crude monoester 11 (44 g). IR (KBr) $v_{max}$ 3065, 3029, 2981, 2928, 2863, 1729, 1642, 1496, 1451, 1378, 1179, 1106, 1025, 996, 915, 853, 737, 696 $cm^{-1}$; $^{1}$HNMR (CDCl$_3$)δ 1.19 (t, J=6.9 Hz, 3 H), 1.75–1.79 (m, 1 H), 1.93–1.97 (m 1 H), 2.22–2.38 (m, 2 H), 2.62–2.63 (m, 1 H), 3.42–3.57 (m, 2 H), 4.04–4.12 (m, 2 H), 4.45 (s 2 H), 5.01–5.02 (m, 2 H), 5.70–5.75 (m, 1 H), 7.23–7.33 (m, 5 H); $^{13}$CNMR (CDCl$_3$)δ 14.00, 31.45, 36.36, 42.05, 59.97, 67.83, 72.76, 116.82, 127.33, 127.36, 127.54, 128.22, 138.20, 175.04; mass spectrum (EI), m/z (rel intensity) 263 (M$^+$–1.1.7), 180 (3.4), 171 (2.6), 156 (12), 155 (11), 131 (3), 128 (23), 107 (14), 101(8), 100 (10), 97 (4), 92 (11), 91 (100), 89 (8), 81 (7), 79 (11), 77 (7), 73 (14), 69 (9), 67 (8), 65 (14).

EXAMPLE 11

2-(2Benzyloxyethyl)-pent-4-en-1-ol (12)

A 1 M solution of lithium aluminium hydride (122 mL, 122 mmol) was added via cannula to a stirred solution of crude ester 11 (44 g), prepared according to Example 10, in dry ether (150 mL). The mixture was stirred for 2 h at room temperature under nitrogen, cooled to 0° C. and water (9 mL) was added dropwise with stirring, followed by 15% NaOH (9 mL) and water (27 mL), which was added dropwise at 0° C. to produce a white precipitate. The precipitate was filtered and washed with ether (2×50 mL). The filtrate was dried over MgSO$_4$. The residue, obtained upon concentration, was subjected to column chromatography on silica gel. Contaminant benzyloxy-2-ethoxy ethanol (12.4 g) was first eluted with ether/hexane (2:1) while the alcohol 12(24 g, 59% based on diethyl allylmalonate) was eluted with 2% methanol in ether. IR (KBr) $v_{max}$ 3404, 3071, 3033, 2930, 2868, 1640, 1498, 1454, 1361, 1202, 1100, 1042, 996, 916, 838, 697 $cm^{-1}$; $^{1}$HNMR (CDCl$_3$) δ 1.63–1.73 (m, 3 H), 2.02–2.15 (m, 2 H), 2.84 (t, J=5.8 Hz, 1 H), 3.45–3.58 (m, 4 H), 4.49 (s, 2 H), 5.00–5.03 (m, 2 H), 5.70–5.85 (m, 1 H), 7.26–7.35 (m, 5 H); $^{13}$CNMR (CDCl$_3$) δ 31.65, 3620, 3891, 53.36, 65.58, 68.66, 73.13, 116.28, 127.69, 127.71, 128.39, 136.75, 137.88: mass spectrum (EI), m/z (rel intensity) 263 (M$^+$+1.10), 203 (1.5), 185 (2.3), 181 (3.5), 143 (2.5), 129 (5), 111 (6), 108 (6), 107 (22), 95 (5), 93 (6), 92 (12), 91 (100), 81 (16), 79 (10), 77 (5), 67 (10), 65 (13).

EXAMPLE 12

4-(1,3-Dioxolan-2-yl)-6-benzyloxyhex-1-ene (14)

Dry DMSO (19.36 mL, 273.6 mmol) in dry CH$_2$Cl$_2$ (35 mL) was added dropwise to a stirred solution of 2 M (COCl)$_2$ (68.40 mL, 136.8 mmol) at −78° C. during 15 min. The alcohol 12 (24 g, 109.44 mmol), prepared according to Example 11 , in dry dichloromethane (50 mL) was then added during 10 min, resulting in a slightly cloudy solution. This was stirred for 30 min at −78° C. and a solution of triethyl amine (79 mL, 547.2 mmol) in dichloromethane (50 mL) was then added dropwise during 15 min. The mixture was stirred for 30 min at −78° C. and 30 min at 0° C. The reaction was quenched by adding water (25 mL) with rapid stirring. The resulting slurry was immediately poured into ether (300 mL) and washed with 20% KHSO$_4$ (2×200 mL). The layers were separated and the aqueous layer was extracted with ether (2×100 mL). The combined organic layers were washed with brine solution (2×100 mL), dried over MgSO$_4$, filtered, and concentrated to afford crude aldehyde 13 (22 g) which was immediately used for protection. A stirred solution of crude 13 (22 g, 101.25 mmol), ethylene glycol (9.4 g, 151.87 mmol), and p-toluenesulfonic acid monohydrate (1 g) in dry benzene (200 mL), contained in a 500 mL round-bottom flask fitted with a Dean Stark trap, was heated at reflux for 12 h. The mixture was cooled to room temperature, the benzene layer was separated, and the aqueous layer was extracted with ether (2×100 mL). The combined organic layers were dried over MgSO$_4$ and filtered. The residue obtained on concentration was purified by column chromatography on silica gel, using ether/hexane (1:1) as eluant, to give acetal 14 (21 g, 73.5%) as an oil. IR (KBr) $v_{max}$ 3066, 3030, 2927, 2881, 1642, 1457, 1400, 1365, 1208, 1156, 1100, 1028, 946, 739, 628 cm$^{-1}$; $^1$HNMR (CDCl$_3$) δ 1.62–1.66 (m, 1 H), 1.79–1.91 (m, 2 H), 2.08–2.11 (m, 1 H), 2.25–2.28 (m, 1 H), 3.54 (t, J=6.9 Hz, 2 H), 3.78–3.90 (m, 4 H), 4.47 (s, 2 H), 4.80 (d, J=3.8 Hz, 1 H), 4.97–5.04 (m, 2 H), 5.77–5.82 (m, 1 H), 7.23–7.34 (m, 5 H); $^{13}$CNMR (CDCl$_3$) δ 28.55, 33.78, 38.33, 64.77, 64.86, 68.40, 72.59, 106.00, 116.04, 127.29, 127.45, 128.16, 136.66, 138.62; mass spectrum (EI), m/z (rel intensity) 262 (M$^+$. 1.6), 171 (4.4), 156 (3.2), 149 (9), 128 (3.3), 114 (2.6), 109 (7), 105 (4.1), 99 (3.6), 92 (3.7), 91 (31), 81 (3.7), 77 (5), 73 (100), 67 (4), 65 (6).

EXAMPLE 13

4-(1,3-Dioxolan-2-yl)-6-benzyloxyhexan-1-ol (15)

A 1 M solution of borane-methyl sulfide complex in dichloromethane (27 mL, 27 mmol) was added dropwise to a stirred solution of the olefin 14 (21 g, 80.36 mmol), prepared according to Example 12, in hexane (60 mL) at 0° C. The mixture was stirred for 3 h at room temperature, then cooled to 0° C., and then absolute ethanol (15 mL) was added dropwise, followed by 15% NaOH (15 mL) and 30% H$_2$O$_2$ (15 mL). The reaction mixture was heated at reflux for 1 h. cooled to room temperature, and poured into water (200 mL). The organic layer was separated, and the aqueous layer was extracted with ether (3×75 mL). The organic layers were combined, dried over MgSO$_4$, and concentrated under reduced pressure. The crude product was chromatographed on a silica gel column, eluting with 2% methanol in ether, to give the alcohol 15 (16.8 g, 74.6%) as a viscous liquid. IR (KBr)ν$_{max}$ 3442, 3034, 2952, 2878, 1458, 1407, 1364, 1206, 1103, 846, 742, 698 cm$^{-1}$; $^1$HNMR (CDCl$_3$) δ 1.36–1.39 (m, 1 H), 1.53–1.64 (m, 4 H), 1.79–1.90 (m, 3 H), 3.53–3.59 (m, 4 H), 3.79–3.92 (m, 4 H), 4.49 (s, 2H), 4.78 (d, J=3.6 Hz, 1 H), 7.25–7.32 (m, 5 H); $^{13}$CNMR (CDCl$_3$) δ 25.38, 29.23, 30.17, 38.19, 62.76, 64.78, 64.84, 68.52, 72.72, 106.49, 127.39, 127.56, 128.23, 138.54: mass spectrum (EI), m/z (rel intensity) 280 (M$^+$.0.02), 235(2.1), 220 (14), 219 (84), 218 (69), 172 (15), 146 (23), 127 (15), 91 (35), 84 (9), 73 (10), 65 (5.5).

EXAMPLE 14

4-(1,3-Dioxolan-2-yl)-6-benzyloxyhexanal (16)

The alcohol (15 (16.8 g, 59.92 mmol), prepared according to Example 13, was oxidized using 2 M (COCl)$_2$ (37.50 mL, 75 mmol), dry DMSO (10.6 mL, 150 mmol), and triethylamine (43 mL, 300 mmol) as for the oxidation of compound 12. Similar work up as for 13 gave a crude product, which was purified by column chromatography eluting with ether/hexane (2:1), to give the aldehyde 16 (4.8 g, 81%) as a colorless oil. IR (KBr)ν$_{max}$ 29.42, 2878, 2725, 1723, 1496, 1434, 1413, 1368, 1211, 1153, 1098, 1031, 951, 742, 661 cm$^{-1}$; $^1$HNMR (CDCl$_3$)δ 1.56–1.86 (m, 5 H), 2.52 (t, J=7.6 Hz, 2H), 3.52–3.57 (m, 2H), 3.79–3.92 (m, 4 H), 4.48 (s, 2 H), 4.75 (d, J=3.3 Hz, 1 H), 7.25–7.34 (m, 5 H), 9.71 (s, 1 H); $^{13}$CNMR (CDCl$_3$)δ 21.48, 29.33, 38.00, 41.71, 64.79, 68.73, 72.82, 106.28, 127.42, 127.55, 128.55, 128.25, 138.48; mass spectrum (EI), m/z (rel intensity) 279 (M$^+$– 1.7.5), 219(7), 171 (15), 144(8), 127(53), 91(31), 83(9), 73(100), 65(4).

EXAMPLE 15

Methyl (3aSR,4RS)-3-benzyl-2,3,3a,4,5,7-hexahydro-4-[(2-ε-(1,3-dioxolan-2-yl)-4-methoxy)-1-butyl]-1H-pyrrolo [2,3-d]carbazole-6-carboxylates (18)

A solution of N$^b$-benzylindoloazapine 17 (3.8 g, 11.36 mmol), prepared according to the procedure described in Kuehne [12] and 4-(1,3-dioxolan-2-yl)-6-methoxyhexanal (8, 2.75 g, 13.63 mmol), prepared according to Example 7, in dry toluene (75 mL) was heated at reflux for 12 h using a Dean-Stark trap filled with 4 A molecular sieves, under nitrogen. The reaction mixture was cooled to room temperature and concentrated on a rotary evaporator. The crude material was flash chromatographed on silica gel, eluting with ether/hexane (1:1), to give the tetracyclic product 18 (4.86 g, 82%) as an inseparable mixture of diastereomers. TLC (SiO$_2$-ether/hexane 2:1) Rf0.32, CAS blue; UV (EtOH) λ$_{max}$ 214, 226, 300, 330; IR (KBr) ν$_{max}$ 3882, 2950, 2877, 1680, 1610, 1478, 1465, 1438, 1281, 1247, 1206, 1118, 1050, 949, 748, 701 cm$^{-1}$; mass spectrum (EI), m/z (rel intensity) 518 (M$^+$.25), 385(21), 332(17), 304(29), 341(12), 160(13), 91(88), 83(9), 73(100).

EXAMPLE 16

Enamine (21)

A solution of the mixture of tetracyclic diastereomers 18 (4.8 g, 9.04 mmol), prepared according to Example 15, in glacial acetic acid (50 mL) was heated to 90° C. NaBH$_4$ (1.03 g, 17 mmol) was added in small portions over a period of 10 min. The mixture was then poured over crushed ice, made basic with NH$_4$OH and extracted with ether (3×50 mL). The organic phase was dried over MgSO$_4$ and concentrated to give an inseparable mixture of cleavamine diasteromers 19 (4.4 g, 91%), which was used directly for hydrogenolysis. A solution of this crude cleaveamine 19 (4.4 g), 10% Pd/C (1 g) in glacial acetic acid (100 mL) was subjected to hydrogenation at 1 atm of H$_2$ for 6 h. The reaction mixture was filtered through a plug of Celite and washed with acetic acid (2×20 mL) and methanol (2×20 mL). The filtrate was basified with cold concentrated NH$_4$OH, and the resulting white precipitate was extracted with ether (4×25 mL). The organic layer was dried over MgSO$_4$ and concentrated to give the secondary amine acetal 20 (3.1 g, 87%), which, for hydrolysis of the acetal function, was dissolved in methanol (35 mL), glacial acetic acid (2 mL), and 10% HCl (35 mL). The mixture was stirred for 12 h at room temperature under nitrogen, cooled to 0° C., and basified with 15% NH$_4$OH in saturated brine. Extraction with ether (4×50 mL), drying over MgSO$_4$, and concentration gave a crude product, which was flash chromatographed on silica gel, eluting with ether/hexane (1:1), to give the enamine 21 (2.02 g, 76%).

EXAMPLE 17

18-Methoxycoronaridine (22)

The enamine 21 (2.0 g, 5.40 mmol), prepared according to Example 16, in dry toluene (30 mL) was heated at 130° C. for 3 h. The reaction mixture was cooled to room temperature and concentrated on a rotary evaporator. Flash chromatography of the crude product on silica gel, eluting with ether/hexane, gave 18-methoxycoronaridine 22 (1.4 g, 70%) as a white solid, UV (EtOH)λ$_{max}$ 228, 278, 285, 294 nm; $^{13}$CNMR δ 175.59, 136.50, 134.80, 128.80, 121.92, 119.21, 118.41, 110.36, 110.00, 70.77, 58.00, 57.60, 54.96, 53.09, 52.58, 51.58, 36.46, 33.90, 33.78, 31.95, 27.33, 22.09.

EXAMPLE 18

Methyl (3aSR,4RS)-3-benzyl-2,3,3a,4,5,7-hexahydro-4-[(2-ε-(1,3-dioxolan-2-yl)-4-benzyloxy)-1-butyl]-1H-pyrrolo[2,3-d]carbazole-6-carboxylates (23a, 23b).

A solution of N$^b$-benzylindoloazepine 17 (5.0 g, 14.95 mmol), prepared according to Kuehne [12], and 4-(1,3- dioxolan-2-yl)-6-benzyloxyhexanal (16, 5.0 g, 17.94 mmol), prepared according to Example 14, in dry toluene (100 m L) was heated at reflux for 12 h, using a Dean-Stark trap filled with 4A molecular sieves under nitrogen. The reaction mixture was cooled to room temperature and concentrated on a rotary evaporator. The concentrate was flash chromatographed on silica gel, eluting with ether/hexane (1:1) to give 23a (4.4 g, 49%) and 23b (4.1 g, 46%).

EXAMPLE 19

Methyl 3-benzyl-1,2,3,4,5,6,7,8-octahydro-5β-[(2-ε-(1,3-dioxolan-2-yl)-4-benzyloxy)-1-butyl]azonino[6,7]indole-7α and 7β carboxylates (24a,24b)

A solution of the tetracycle 23a (4.0 g, 6.73 mmol), prepared in Example 18, in glacial acetic acid (40 mL) was heated at 90° C. $NaBH_4$ (0.77 g, 20 mmol) was added in small portions over a period of 10 min. The mixture was then poured over crushed ice, made basic with $NH_4OH$, and extracted with ether (3×50 mL). The organic phase was dried over $MgSO_4$ and concentrated. Flash chromatography of the crude materials on silica gel, eluting the ether/hexane (2:1), gave 24a (3.25 g, 81%) and 24b (0.65 g, 16%). Analogously, the tetracycle 23b was reduced to the corresponding cleavamine esters 24c and 24d.

EXAMPLE 20

Enamine (26)

A solution of cleaveamines 24a and 24b (2.7 g, 4.51 mmol) and 10% Pd/C (1 g) in ethyl acetate (50 mL) and glacial acetic acid (5 mL) was subjected to hydrogenolysis at 1 atm of $H_2$ for 16 hours. The reaction mixture was filtered through a plug of Celite and washed with acetic acid (2×20 mL) and methanol (2×20 m L). The filtrate was basified with cold concentrated $NH_4OH$, and the resulting white precipitate was extracted with ether (4×25 mL). The organic layer was dried over $MgSO_4$ and concentrated to give the secondary amine acetal 25 (1.75 g, 77%), which was dissolved in methanol (16 mL), glacial acetic acid (1 mL), and 10% HCl (16 mL). The mixture was stirred in a round bottom flask covered with aluminum foil for 24 hours, at room temperature under nitrogen, then cooled to 0° C. and basified with 15% $NH_4OH$ in saturated brine. Extraction with ether (4×50 mL), drying over $MgSO_4$, and concentration gave a crude product, which was flash chromatographed on silica gel, eluting with ether/hexane (1:1), to give the enamine 26 (1.3 g, 86%).

EXAMPLE 21

18-Benzyloxycoronaridine (27)

The enamine 26 (2.0 g, 5.40 mmol), prepared in Example 20, in dry toluene (30 mL) was heated at 130° C. for 3 hours. The reaction mixture was cooled to room temperature and concentracted on a rotary evaporator. Flash chromatography of the crude product on silica gel, eluting with ether/hexane, gave the title product 27 (1.4 g, 70%) as a white solid. UV (EtOH) $\lambda_{max}$ 214, 234, 278, 286, 294 nm; $^{13}$CNMR δ 175.44, 138.60, 136.52, 135.47, 128.66, 128.15, 127.52, 127.45, 121.76, 119.07, 118.27, 110.31, 110.13, 72.80, 68.38, 57.51, 54.86, 53.06, 52.56, 51.64, 36.33, 34.12, 33.79, 31.87, 27.22, 21.94.

EXAMPLE 22

Albifloranine (28)

A mixture of 27 (1 g), prepared according to Example 21, 10% Pd/C (1 g), and ammonium formate (2 g) in dry methanol (50 mL) was heated at reflux for 4 hours and then cooled to room temperature. The mixture was filtered through a Celite pad, and the filtrate was concentrated. The residue was flash chromatographed on silica gel, eluting with 1% MeOH in ether, to give racemic albifloranine (28, 0.6 g, 75%), $^{13}$CNMR 175.17, 135.87, 135.55, 128.37, 121.92, 119.17, 118.25, 110.39, 109.97, 59.27, 57.93, 54.62, 52.90, 52.90, 52.68, 51.55, 36.32, 36.26, 34.62, 29.26, 26.97, 21.48.

EXAMPLE 23

16-Hydroxymethyl-18-methoxyibogamine (29)

A solution of 2.0 g (5.4 mmol) of 18-methoxycoronaridine (22), prepared in accordance with Example 17, in 100 mL of dry tetrahydrofuran and 205 mg (5.4 mmol) of $LiAlH_4$ was heated at reflux for 4 hours. Addition of 10 g of sodium sulfate hexahydrate to the cooled mixture and stirring for 5 hours, followed by filtration and concentration provided the carbinol 29 (2.0 g, 99% yield), $^{13}$CNMR δ 135.45, 128.56, 121.15, 118.83, 117.98, 111.05, 110.33, 71.05, 65.81, 58.57, 54.41, 53.32, 47.67, 36.54, 34,35, 32.19, 30.61, 27.74, 21.83, 15.23.

EXAMPLE 24

Drugs 18-methoxycoronaridine was prepared by the method described in Example 17, above. Ibogaine hydrochloride and harmaline hydrochloride were purchased from the Sigma Chemical Company (St. Louis, Mo.). The R- and S-enantiomers of ibogamine and coronaridine (structures shown in [14]) were prepared according to the methodology of Bornmann [7] and Kuehne [13]. Racemic desethylcoronaridine were synthesized using the procedures described in Bornmann [7]. Tabernanthine was supplied by P. Potier, CNRS, Institute of Chemistry of Natural Substances, Gif-sur-Yvette, France. All drugs were administered intrapertioneally; doses are expressed as the hydrochloride salts. Different drugs and doses (or saline) were administered to different groups of rats; rats were injected fifteen minutes before a morphine or cocaine self-administration session.

EXAMPLE 25

Subjects and Apparatus

The subjects were naive female Sprague-Dawley (Taconic, Germantown, N.Y.) rats approximately 3 months old and weighing 230–250 g at the beginning of the experiment; female rats were used because they grow at a much slower rate than males and are less likely than males to outgrow their intravenous cannulas. Rats were housed singly in Wahmann hanging cages and maintained on a normal light/dark cycle (lights on/off at 7:00 a.m./7:00 p.m.). All self-administration testing was conducted in twelve BRS/LVE operant test cages, each enclosed in a sound attenuated cubicle. Responses on either of two levers (mounted 15 cm apart on the front wall of each test cage) were recorded on an IBM compatible 386 computer with a Med Associates, Inc. interface. The intravenous self-administration system consisted of polyethylene-silicone cannulas constructed according to the design of Weeks [15], BRS/LVE harnesses and commutators, and Harvard Apparatus infusion pumps (no. 55-222).

EXAMPLE 26

Self-Administration Procedures

Shaping of the bar-press response was initially accomplished by training rats to bar-press for water. Cannulas were then implanted in the external jugular vein according to procedures described by Weeks [15]. Self-administration testing began with a single 24-h session followed by daily 1-h sessions. 5 days (Monday–Friday) a week: rats were tested about the same time each day, during the middle of the light cycle. Depending upon the group, a lever-press response produced either a 20 $\mu$l (morphine) or 50 $\mu$l (cocaine) infusion of drug solution (0.01 mg of morphine sulfate or 0.1 mg of cocaine hydrochloride) in about 0.2 (morphine) or 0.5 (cocaine) seconds. Since all rats generally weighed 250±20 g, each response delivered approximately 0.04 mg/kg of morphine or 0.4 mg/kg of cocaine; these doses are about two to four times the threshold doses required for maintaining self-administration behavior [16.17]. One non-contingent drug infusion was administered at the beginning of each session. Experiments to assess the effects of the iboga and harmala alkaloids were begun when baseline self-administration rates stabilized ($\leq 10\%$ variation from one day to the next across 5 days), usually after two weeks of testing.

EXAMPLE 27

Tremor Testing Procedures

Whole body tremors were assessed in two ways. Direct visual observations were made of rats confined in a Plexiglas cylindrical (9 inches in diameter) enclosure; videotapes were sometimes made so that initial observations could be confirmed at a later time. Tremors were rated as absent, moderate or intense on a minute to minute basis for 30 min. beginning 15 min. after drug administration. An automated and quantitative technique, based on a method originally designed for mice by other investigators [18], was also developed and utilized. Briefly, a PLEXIGLAS™ enclosure was mounted on an audio speaker, the output of which was connected to a Hewlett-Packard 3392A integrator: the sensitivity of the integrator was adjusted such that random locomotor activity was generally ignored while large peaks representing tremors could be readily identified. Tremors were recorded and counted for 30 min. beginning 15 min. after drug administration.

EXAMPLE 28

Drug Self-Administration

Figure 2A:
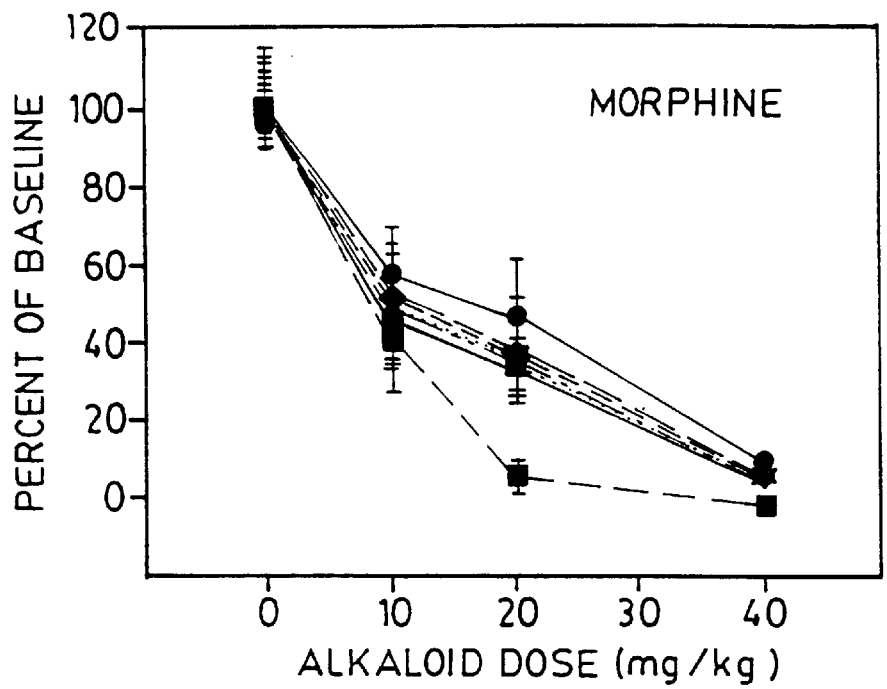
FIG. 2 is a plot of the acute effects of ibogaine, harmaline, tabernanthine, desethylcoronaridine, R-coronaridine, S-coronaridine, R-ibogamine, and S-ibogamine on morphine and cocaine self administration. Each data point is the mean (±S.E.) from 3–8 rats. Baseline was calculated as the average for the three sessions preceding drug or saline (0 mg/kg) administration. All doses of all drugs had significant effects (ANOVA and t-tests, $P<0.05-0.001$).
Figure 2B:
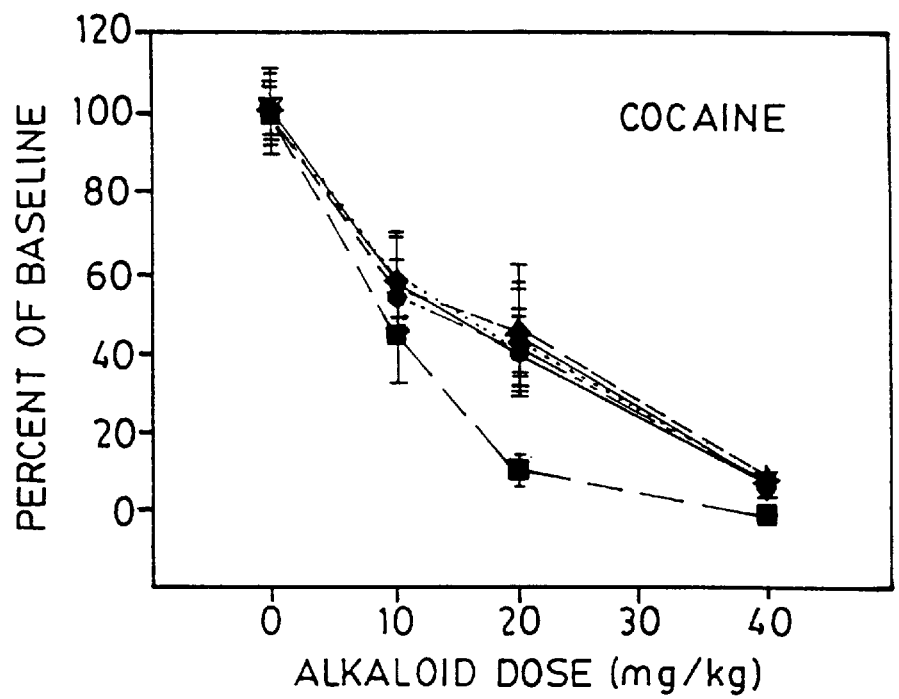
Figure 3A:
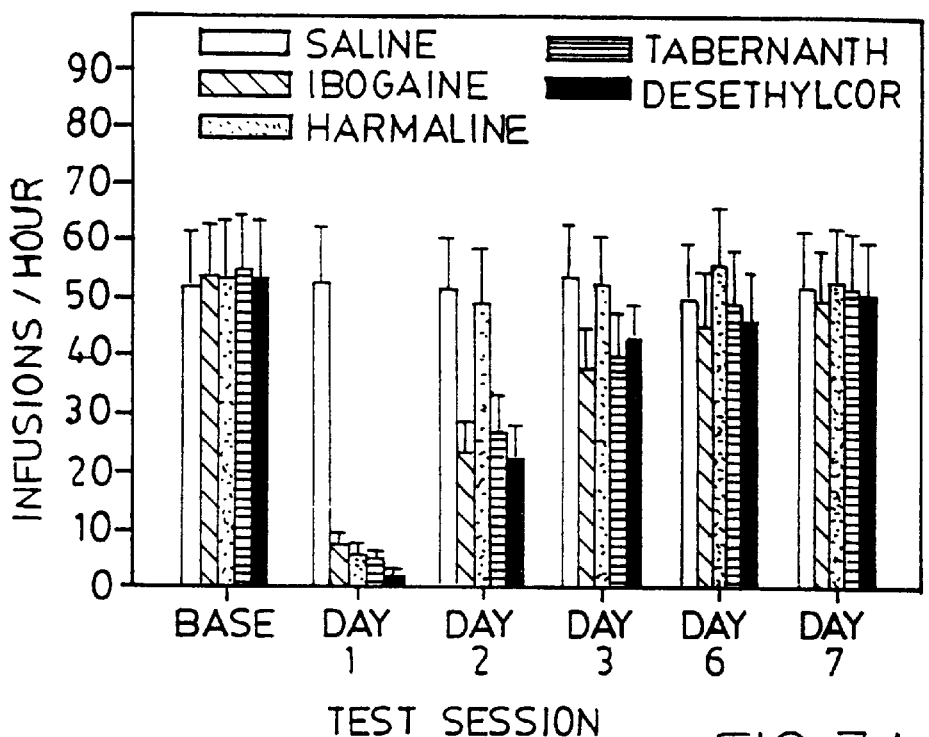
FIG. 3 is a bar graph showing the aftereffects of alkaloids (20 mg/kg for desethylcoronaridine and 40 mg/kg for all others) on morphine self administration. Each data point is the mean (±S.E.) from 5–8 rats. 'Base' refers to the baseline rate of responding, calculated as the average for the three sessions preceding drug or saline treatment. There were significant effects on Day 1 for all drugs and on day two for 18-methoxycoronaridine, ibogaine, tabernanthine, desethylcoronaridine, R-coronaridine, and R-ibogamine (ANOVA and t-tests. $P<0.05-0.001$).
Figure 3B:
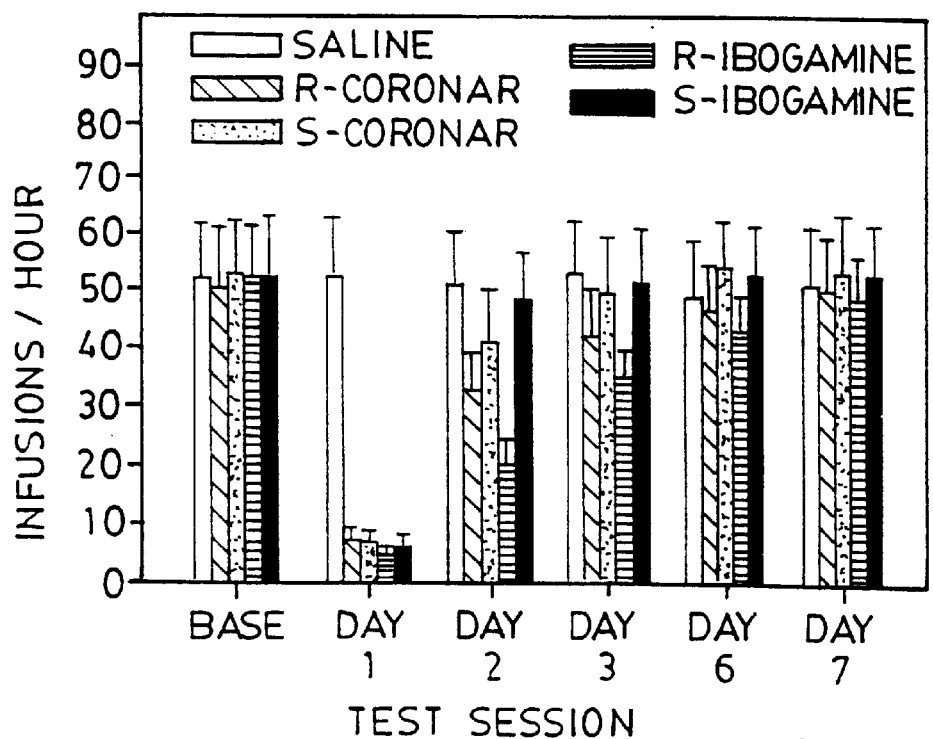
Figure 3C:
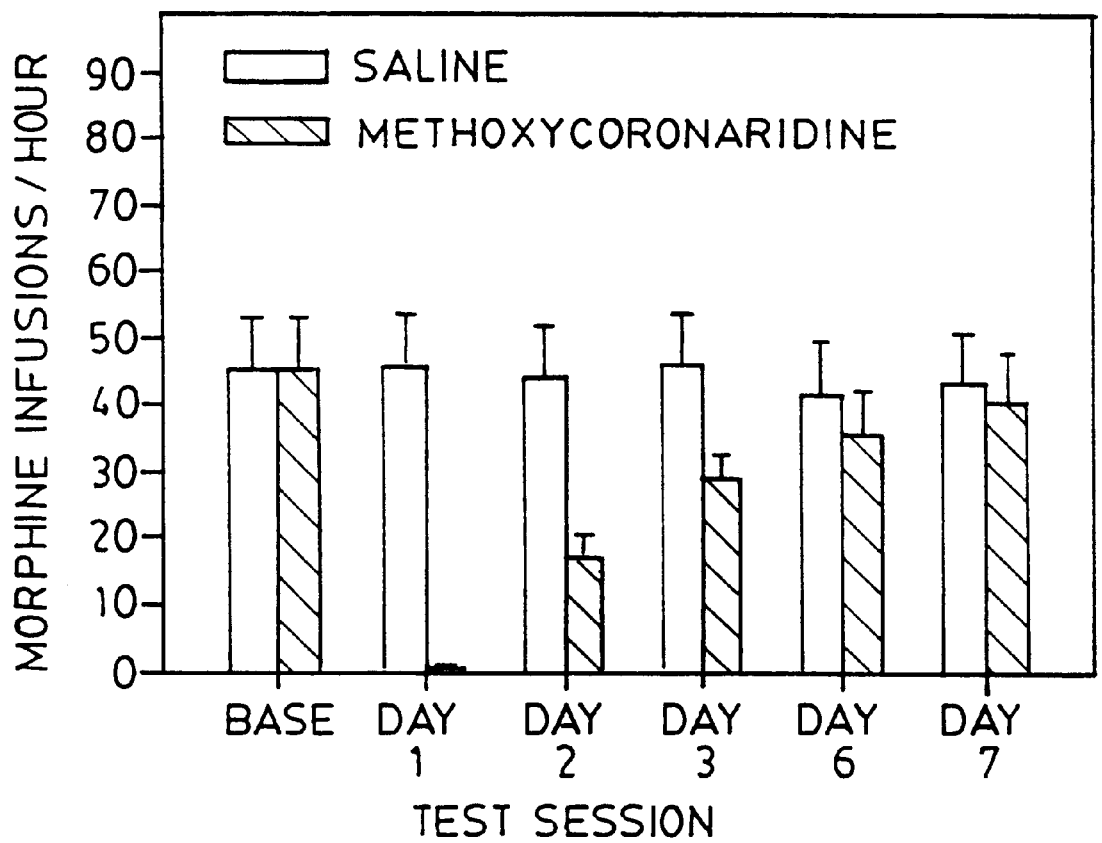
Figure 4A:
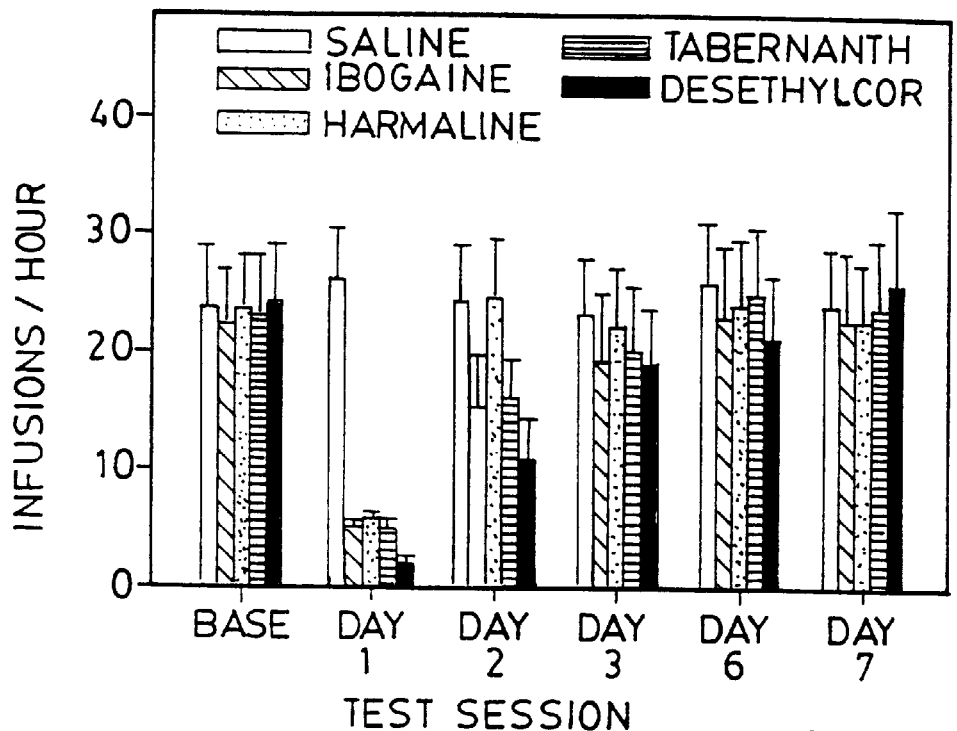
FIG. 4 is a bar graph showing the aftereffects of alkaloids (20 mg/kg for desethylcoronaridine and 40 mg/kg for all others) on cocaine self administration. Each data point is the means (±S.E.) from 4–8 rats. 'Base' refers to the baseline rate of responding, calculated as the average for the three sessions preceding drug or saline treatment. There were significant effects on Day 1 for all drugs and on day two for 18-methoxycoronaridine, ibogaine, tabernanthine, desethylcoronaridine, R-coronaridine, and R-ibogamine (ANOVA and t-tests, $P<0.05-0.001$).
Figure 4B:
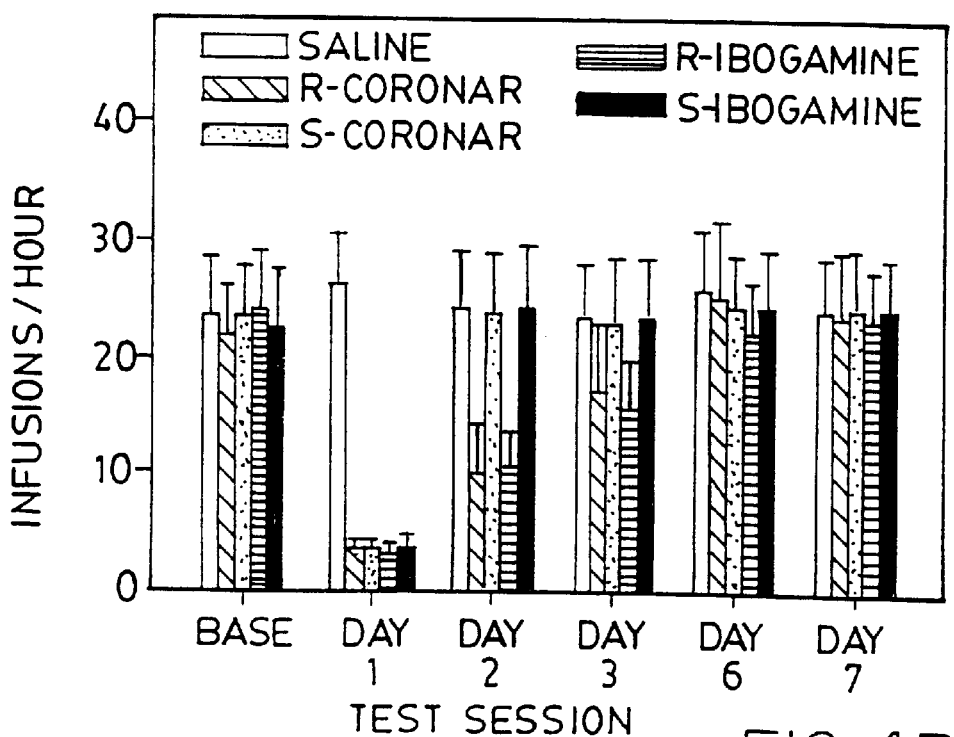
Figure 4C:
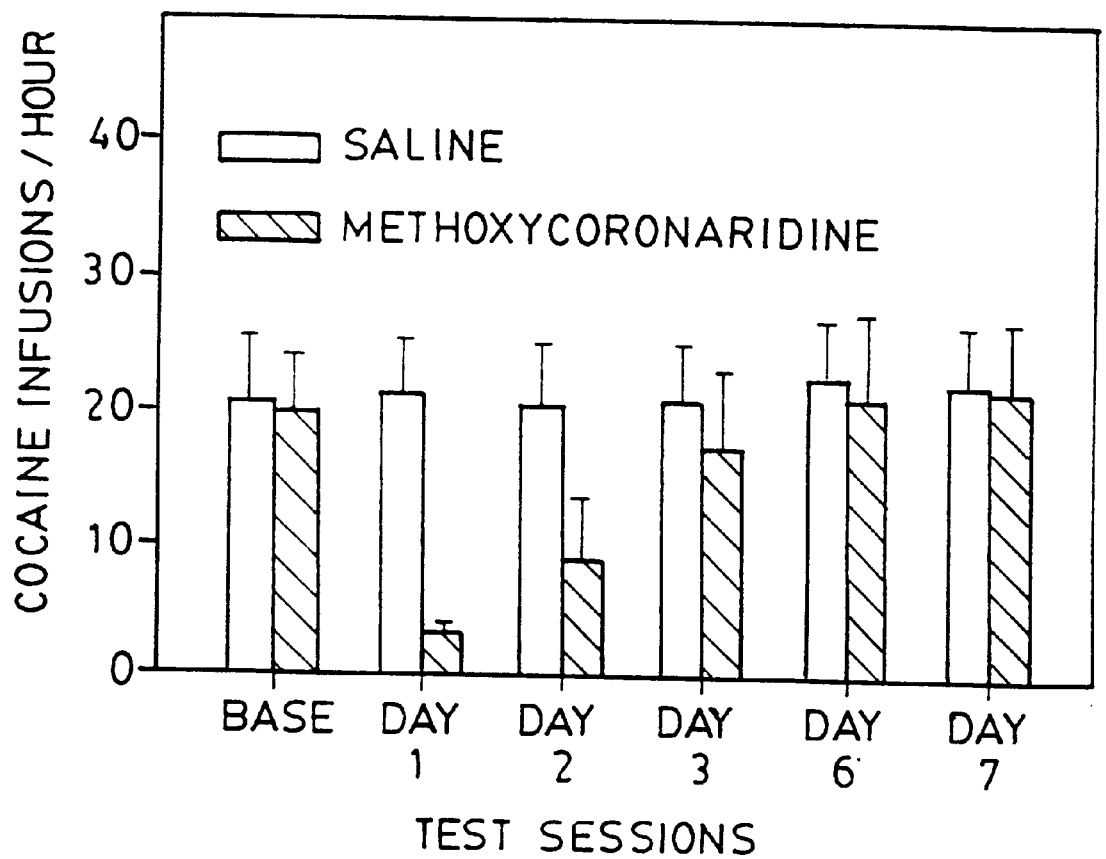

FIGS. 1 and 2 shows the initial acute effects of 18-methoxycoronaridine and all of the remaining alkaloids, respectively, on morphine and cocaine self-administration. Each drug produced a dose-related depression of morphine and cocaine intake (ANOVA, $P<0.001$ in every case). The potencies of the 18-methoxycoronaridine and the other alkaloids were very similar and, as shown in FIG. 2, cannot be distinguished, with the exception that desethylcoronaridine was approximately twice as potent as any of the other drugs. FIG. 3 shows that ibogaine (40 mg/kg), R-ibogamine (40 mg/kg), R-coronaridine (40 mg/kg), tabernanthine (40 mg/kg) and desethylcoronaridine (20 mg/kg), each administered for the first time, depressed morphine intake for at least a day afterwards. FIG. 4 shows similar results for cocaine. In each of these cases, a group×days interaction was significant ($P<0.05$ in a two-way ANOVA), and paired t-tests with baseline values were significant ($P<0.05$–0.01) for days 1 and 2 in the indicated treatment groups. The extent of these aftereffects (one or more days later) on drug self-administration varied substantially from rat to rat; responses beyond a day later (Day 2) ranged from no further effect to a prolonged depression of morphine or cocaine intake, lasting up to several weeks in a few rats. In general, the aftereffects on cocaine intake were more variable than those on morphine intake.

Figure 5:
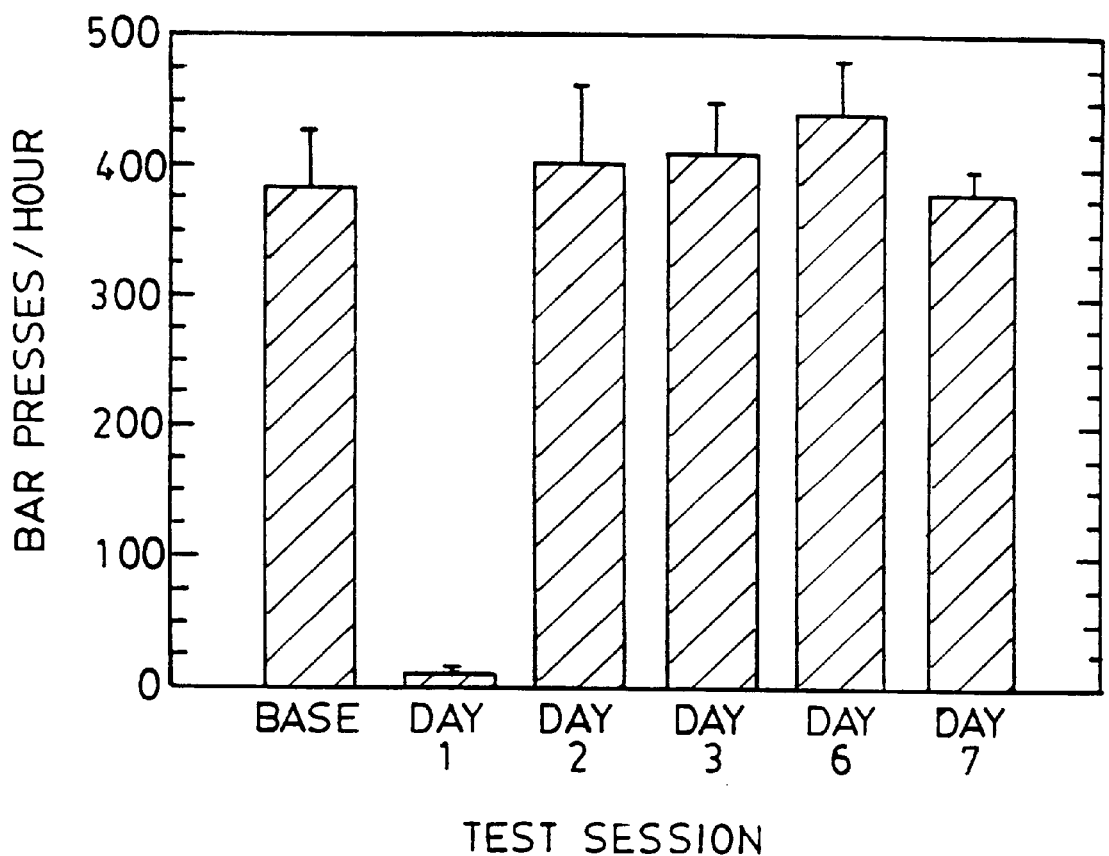
FIG. 5 is a bar graph showing the aftereffects of ibogaine (40 mg/kg) on bar pressing for water; presession administration on Day 1. Each data point is the mean (±S.E.) from six rats. 'Base' refers to the baseline rate of responding, calculated as the average for the three sessions preceding ibogaine treatment. There was a significant effect on Day 1 ($P<0.001$, t-test) but not thereafter.
Figure 6:
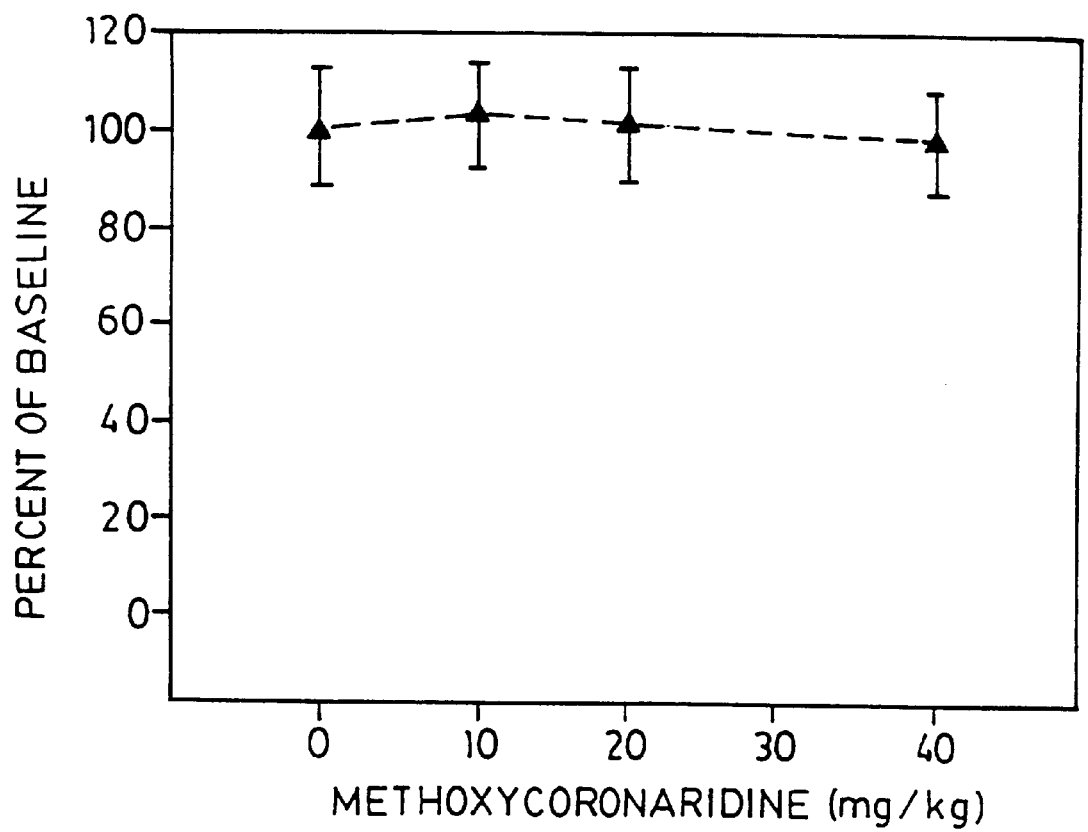
FIG. 6 is a line graph showing the acute effects of 18-methoxycoronaridine on bar pressing for water administered intraperitoneally ("IP") 15 minutes before a one hour test session. No acute affects are noted.

The effects of ibogaine and 18-methoxycoronaridine on motivated behavior were studied [1] by monitoring water bar pressing. Ibogaine (40 mg/kg) acutely depressed bar pressing for water for the first hour following ibogaine administration but bar pressing for water recovered to normal by the second day (FIG. 5). As shown in FIG. 6, this acute, short-term decrease in motivated behavior was not observed following 18-methoxycoronadine administration.

EXAMPLE 29

Tremorigenic Effects

Ibogamine (20–40 mg/kg), harmaline (10–40 mg/kg) and desethycoronaridine (10–40 mg/kg) were obviously tremorigenic for 3–4 h and no attempt was made to compare these drugs quantitatively. However, visual observations and videotape recordings of 18-methoxycoronaridine (40 mg/kg) and both R- and S-enantiomers of both ibogamine (40 mg/kg) and coronaridine (40 mg/kg) indicated very little if any tremorigenic activity. The effects of these latter drugs were therefore assessed using the automated testing procedure developed to quantitate tremors. Ibogains (40 mg/kg) and saline (1 ml/kg) were used as positive and negative controls, respectively. While ibogaine produced a significant increase in movements indicative of tremors, the 18-methoxycoronaridine and the ibogamine and coronaridine enantiomers had no effects that differed significantly from the effects of saline.

EXAMPLE 30

Neurotoxicity Studies

In a study similar to that conducted by O'Hearn and Molliver [5], female Sprague Dawley (Charles River) rats were given IP injections of ibogaine and allowed to survive seven days after the last injection. Purkinje cell degeneration was evaluated with a Fink Heimer II stain; enhanced glial cell activity, with a GFAP antibody stain.

One set of animals received an ibogaine dose tested by O'Hearn and Molliver: 100 mg/kg per day for three consecutive days. All of these animals displayed bilaterally symmetric, parasagittal strips of Purkinje cell degeneration. The degeneration was more extensive than suggested by O'Hearn and Molliver, consistently occurring in the medial simple fobule and Crus 1 as well as the vermis and intermediate regions of lobules 5, 6, and 7. A second set of animals received a dose of 18-methoxycoronaridine (100 mg/kg). No evidence of Purkinje cell degeneration was found in these animals.

Although the invention has been described in detail for the purpose of illustration, it is understood that such detail is solely for that purpose, and variations can be made therein by those skilled in the art without departing from the spirit and scope of the invention which is defined by the following claims.

LIST OF REFERENCES CITED

1. Glick, et al., Effects and Aftereffects of Ibogaine on Morphine Self-administration in Rats, *Eur J. Pharmacol.*, 195:341–345 (1991).
2. Cappendijk, et al., Inhibitory Effects of Ibogaine on Cocaine Self-administration in rats, *Eur J. Pharmacol.*, 241:261–265 (1993).

3. de Montigny, et al., Rhythmic Activity Induced by Harmaline in the Olivo-cerebello-bulbar System of the Cat. *Brain Res.*, 53:81–95 (1973).
4. Llinas, et al., The Olivo-cerebellar System: Functional Properties as Revealed by Harmaline-induced Tremor, *Exp. Brain Res.*, 18:69–87 (1973).
5. O'Hearn, et al., Degeneration of Purkinje Cells in Parasagittal Zones of the Cerebellar Vermis After Treatment with Ibogaine or Harmaline, *Neuroscience*, 55:303–310 (1993).
6. O'Hearn, et al., Ibogaine Induces Glial Activation in Parasaggital Zones of the Cerebellum, *Neuro Report*, 4:299–302 (1993).
7. Bornmann, et al., *J. Org. Chem.*, 57:1752 (1992).
8. Kuehne, et al., *J. Org. Chem.*, 58:4147 (1993).
9. Kuehne, et al., *J. Org. Chem.*, 43:3705 (1978).
10. Kuehne, et al., *J. Org. Chem.*, 44:1063 (1979).
11. Kuehne, et al., *J. Org. Chem.*, 45:3259 (1980).
12. Kuehne, et al., *J. Org. Chem.*, 50:919 (1985).
13. Kuehne, et al., *J. Org. Chem.*, 56:513 (1991).
14. Deecher, et al., Mechanisms of Action of Ibogaine and Harmaline Congeners Based on Radioligand Binding Studies, *Brain Res.*, 571:242–247 (1992)
15. Weeks, Long-term Intravenous Infusion, pp. 155–168 in *Methods of Psychobiology*, Vol, 2, R. D. Myers, ed., Academic Press, New York, 1992.
16. Glick, et al., Changes in Morphine Self-administration after Brainstem Lesions in Rats, *Psychopharmacology*, 52:151–156 (1977).
17. Glick, et al., Food Deprivation and Stimulant Self-administration in Rats: Differences between Cocaine and d-amphetamine. *Psychopharmacology*, 91:372–374 (1987).
18. Remington, et al., A Simple Method for Quantifying Tremor in Rodents, *Pharmacol. Biochem. Behav.*, 4:721–723 (1976).

What is claimed is:

1. A compound having the formula:

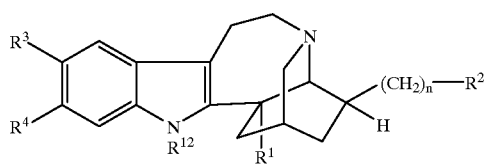

wherein
n is from 0 to 8;
$R^1$ is $CH_2OH$, $CH(OH)R^5$, $CH_2OR^5$, $CO_2R^5$, $C(O)NH_2$, $C(O)NHR^5$, $C(O)NR^5R^6$, $C(O)NHNH_2$, $C(O)NHNHR^5$, $C(O)NHNR^5R^6$, $C(O)NR^5NH_2$, $C(O)NR^5NHR^6$, $C(O)NR^5NR^6R^7$, $C(O)NHNH(C(O)R^5)$, $C(O)NHNR^5(C(O)R^6)$, $C(O)NR^5NH(C(O)R^6)$, $C(O)NR^5NR^6(C(O)R^7)$, or $C(O)R^5$;
$R^2$ is H, unsubstituted or substituted alkyl, YH, $YR^8$, $YC(O)R^8$, $C(O)YR^8$, $C(O)NH_2$, $C(O)NHR^8$, $C(O)NR^8R^9$, $NH_2$, $NHR^8$, $NR^8R^9$, $NHC(O)R^8$, $NR^8C(O)R^9$;
$R^3$ and $R^4$ are the same or different and are selected from the group consisting of H, halogens, unsubstituted or substituted alkyl, OH, $OR^{10}$, $NH_2$, $NHR^{10}$, $NR^{10}R^{11}$, $NHC(O)R^{10}$, or $NR^{10}C(O)R^{11}$;
$R^5$, $R^6$, $R^7$, $R^8$, $R^9$, $R^{10}$, $R^{11}$ are the same or different and are selected from the group consisting of unsubstituted alkyl and substituted alkyl;
$R^{12}$ is selected from the group consisting of H, unsubstituted alkyl, and substituted alkyl; and Y is O or S;
provided that when n is 0, $R^2$ is substituted alkyl other than $CH(OH)CH_3$;
further provided that when n is 2, $R^2$ is OH, $R^{12}$ is H, and both $R^3$ and $R^4$ are H, $R^1$ is not $CO_2CH_3$; and
further provided that when n is 2, $R^2$ is H, $R^{12}$ is H, and $R^3$ and $R^4$ are the same or different and are selected from the group consisting of H and $OCH_3$, $R^1$ is not $CO_2CH_3$;
or a pharmaceutically acceptable salt thereof.

2. A compound according to claim 1, wherein $R^3$ and $R^4$ are H.
3. A compound according to claim 1, wherein $R^{12}$ is H.
4. A compound according to claim 1, wherein $R^1$ is $CO_2R^5$.
5. A compound according to claim 4, wherein $R^5$ is $CH_3$.
6. A compound according to claim 1, wherein $R^1$ is $CH_2OH$.
7. A compound according to claim 1, wherein n is 2 and $R^2$ is $YR^8$.
8. A compound according to claim 7, wherein Y is O.
9. A compound according to claim 8, wherein $R^8$ is $CH_3$.
10. A compound according to claim 8, wherein $R^8$ is $CH_2Ph$.
11. A compound according to claim 8, wherein $R^8$ is $CH_2OCH_2CH_2OCH_3$.
12. A compound according to claim 1, wherein n is 2 and $R^2$ is YH.
13. A compound according to claim 12, wherein Y is O.
14. A compound according to claim 1, wherein n is 2 and $R^2$ is $YC(O)R^8$.
15. A compound according to claim 14, wherein Y is O.
16. A compound according to claim 15, wherein $R^8$ is $(CH_2)_mCH_3$ and wherein m is from 0 to 20.
17. A compound according to claim 16, wherein m is 10.
18. A compound according to claim 1, having the formula:

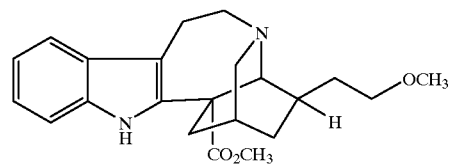

19. A compound according to claim 1, having the formula:

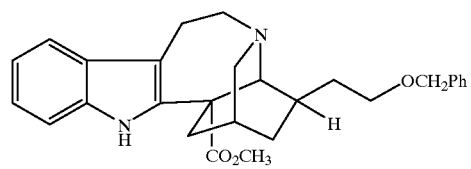

20. A compound according to claim 1, having the formula:

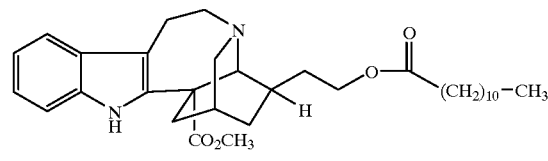

21. A compound according to claim 1, having the formula:

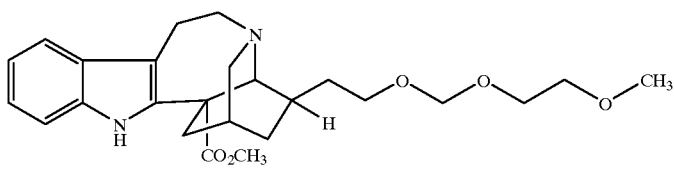

22. A compound according to claim 1, having the formula:

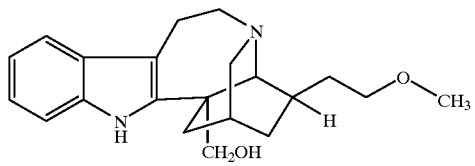

23. A composition comprising a compound according to claim 1 and a pharmaceutically acceptable carrier.

24. A method of treating a subject's addiction to an addictive substance, said method comprising:

administering to a subject addicted to an addictive substance an effective amount of a compound having the formula:

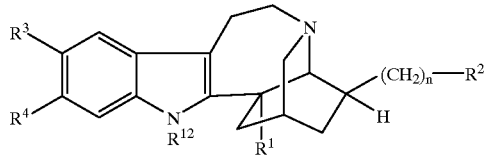

wherein n is from 0 to 8;

$R^1$ is $CH_2OH$, $CH(OH)R^5$, $CH_2OR^5$, $CO_2R^5$, $C(O)NH_2$, $C(O)NHR^5$, $C(O)NR^5R^6$, $C(O)NHNH_2$, $C(O)NHNHR^5$, $C(O)NHNR^5R^6$, $C(O)NR^5NH_2$, $C(O)NR^5NHR^6$, $C(O)NR^5NR^6R^7$, $C(O)NHNH(C(O)R^5)$, $C(O)NHNR^5(C(O)R^6)$, $C(O)NR^5NH(C(O)R^6)$, $C(O)NR^5NR^6(C(O)R^7)$, CN, or $C(O)R^5$;

$R^2$ is H, unsubstituted or substituted alkyl, YH, $YR^8$, $YC(O)R^8$, $C(O)YR^8$, $C(O)NH_2$, $C(O)NHR^8$, $C(O)NR^8R^9$, $NH_2$, $NHR^8$, $NR^8R^9$, $NHC(O)R^8$, or $NR^8C(O)R^9$;

$R^3$ and $R^4$ are the same or different and are selected from the group consisting of H, halogens, unsubstituted or substituted alkyl, OH, $OR^{10}$, $NH_2$, $NHR^{10}$, $NR^{10}R^{11}$, $NHC(O)R^{10}$, or $NR^{10}C(O)R^{11}$;

$R^5$, $R^6$, $R^7$, $R^8$, $R^9$, $R^{10}$, and $R^{11}$ are the same or different and are selected from the group consisting of unsubstituted alkyl and substituted alkyl;

$R^{12}$ is selected from the group consisting of H, unsubstituted alkyl, and substituted alkyl; and Y is O or S;

provided that when n is 0, $R^2$ is selected from the group consisting of H, substituted alkyl, and unsubstituted alkyl; and further provided that when n is 2, $R^2$ is H, $R^{12}$ is H, and both $R^3$ and $R^4$ are H, $R^1$ is not $CO_2CH_3$;

or a pharmaceutically acceptable salt thereof.

25. A method according to claim 4, wherein the addictive substance is selected from the group consisting of opiates, stimulants, depressants, barbituates, and combinations thereof.

26. A method according to claim 5, wherein the addictive substance is an opiate.

27. A method according to claim 6, wherein the opiate is heroin.

28. A method according to claim 5, wherein the addictive substance is a stimulant.

29. A method according to claim 8, wherein said stimulant is cocaine.

30. A method according to claim 4, wherein the addictive substance is ethanol.

31. A method according to claim 4, wherein the addictive substance is nicotine.

32. A method according to claim 24, wherein $R^3$ and $R^4$ are H.

33. A method according to claim 24, wherein $R^{12}$ are H.

34. A method according to claim 24, wherein $R^1$ is $CO_2R^5$.

35. A method according to claim 34, wherein $R^5$ is $CH_3$.

36. A method according to claim 24, wherein $R^1$ is $CH_2OH$.

37. A method according to claim 24, wherein n is 2 and $R^2$ is $YR^8$.

38. A method according to claim 37, wherein Y is O.

39. A method according to claim 38, wherein $R^8$ is $CH_3$.

40. A method according to claim 37, wherein $R^8$ is $CH_2Ph$.

41. A method according to claim 38, wherein $R^8$ is $CH_2OCH_2CH_2OCH_3$.

42. A method according to claim 24, wherein n is 2 and $R^2$ is YH.

43. A method according to claim 42, wherein Y is O.

44. A method according to claim 24, wherein n is 2 and $R^2$ is $YC(O)R^8$.

45. A method according to claim 44, wherein Y is O.

46. A method according to claim 45, wherein $R^8$ is $(CH_2)_mCH_3$ and wherein m is from 0 to 20.

47. A method according to claim 46, wherein m is 10.

48. A method according to claim 24, wherein the compound has the formula:

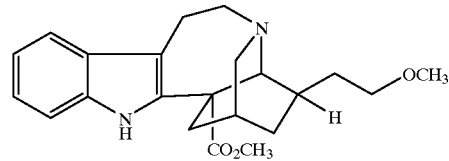

49. A method according to claim 24, having the formula:

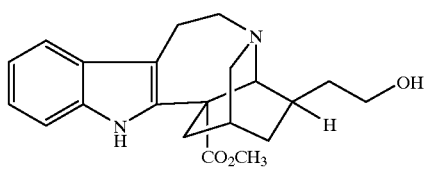

50. A method according to claim 24, wherein the compound has the formula:

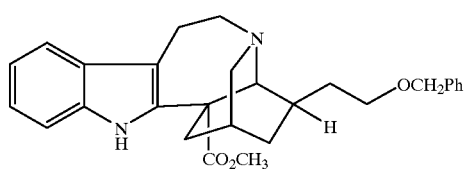

51. A method according to claim 24, wherein the compound has the formula:

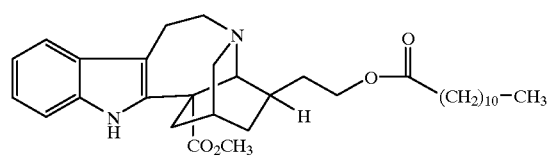

52. A method according to claim 24, wherein the compound has the formula:

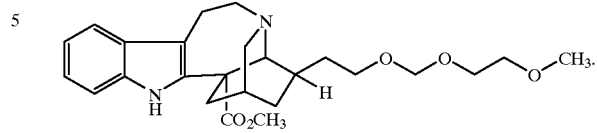

53. A method according to claim 24, wherein the compound has the formula:

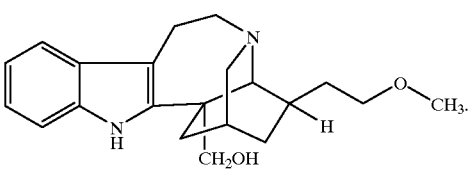

54. A method according to claim 24, wherein the compound is administered in a dose of from about 1.0 to about 80 mg per kilogram of the subject's mass.

* * * * *

UNITED STATES PATENT AND TRADEMARK OFFICE
CERTIFICATE OF CORRECTION

PATENT NO. : 6,211,360 B1
DATED : April 3, 2001
INVENTOR(S) : Glick et al.

It is certified that error appears in the above-identified patent and that said Letters Patent is hereby corrected as shown below:

Column 30,
Line 12, delete "4" and insert -- 24 --.
Line 16, delete "5" and insert -- 25 --.
Line 18, delete "6" and insert -- 26 --.
Line 20, delete "5" and insert -- 25 --.
Line 22, delete "8" and insert -- 28 --.
Line 24, delete "4" and insert -- 24 --.
Line 26, delete "4" and insert -- 24 --.

Signed and Sealed this

Third Day of August, 2004

JON W. DUDAS
*Acting Director of the United States Patent and Trademark Office*